US011330686B2

(12) United States Patent
Peeters et al.

(10) Patent No.: US 11,330,686 B2
(45) Date of Patent: May 10, 2022

(54) CYAN ENRICHED WHITE LIGHT

(71) Applicant: SIGNIFY HOLDING B.V., Eindhoven (NL)

(72) Inventors: Martinus Petrus Joseph Peeters, Weert (NL); Rene Theodorus Wegh, Veldhoven (NL); Remy Cyrille Broersma, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 17/270,487

(22) PCT Filed: Aug. 26, 2019

(86) PCT No.: PCT/EP2019/072674
§ 371 (c)(1),
(2) Date: Feb. 23, 2021

(87) PCT Pub. No.: WO2020/043649
PCT Pub. Date: Mar. 5, 2020

(65) Prior Publication Data
US 2021/0329757 A1 Oct. 21, 2021

(30) Foreign Application Priority Data
Aug. 31, 2018 (EP) .................................. 18191993

(51) Int. Cl.
*H05B 45/20* (2020.01)
*F21V 9/30* (2018.01)
*A61M 21/00* (2006.01)

(52) U.S. Cl.
CPC .............. *H05B 45/20* (2020.01); *F21V 9/30* (2018.02); *A61M 21/00* (2013.01); *A61M 2021/0044* (2013.01)

(58) Field of Classification Search
CPC ........ H05B 45/10; H05B 45/20; H05B 47/10; H05B 47/105; F21V 9/30; A61M 21/00; A61M 2021/0044; A61N 5/0618
See application file for complete search history.

(56) References Cited

U.S. PATENT DOCUMENTS 9,039,746 B2   5/2015   Van De Ven et al.
9,661,715 B2   5/2017   Van De Ven et al.
(Continued)

FOREIGN PATENT DOCUMENTS

DE    102014113976 A1   4/2015
WO      2016146688 A1   9/2016
(Continued)

OTHER PUBLICATIONS

R.J. Lucas, et al., "Measuring and using light in the melanopsin age", Trends in Neurosciences, vol. 37, No. 1, Jan. 2014, pp. 1-9.

*Primary Examiner* — Haissa Philogene
(74) *Attorney, Agent, or Firm* — Daniel J. Piotrowski

(57) ABSTRACT

The invention provides a light generating device (100) configured to generate in a first control mode device light (101), wherein the light generating device (100) comprises (i) a first source (210) of first light (211), and (ii) a second source (220) of second light (221), different from the first light (211), wherein the second light (221) comprises cyan-like light having a wavelength selected from the range of 470-520 nm, wherein the device light (101) comprises the first light (211) and the second light (221), and wherein in the first control mode the first light (211) is white light and the device light (101) is white light enriched with cyan-like light.

15 Claims, 10 Drawing Sheets

(56) References Cited

U.S. PATENT DOCUMENTS

| | | | |
|---|---|---|---|
| 10,212,766 B2* | 2/2019 | Gordin | H05B 33/08 |
| 2004/0156192 A1 | 8/2004 | Kerr et al. | |
| 2015/0195885 A1 | 7/2015 | Van De Ven et al. | |
| 2017/0086274 A1* | 3/2017 | Soler | H05B 45/10 |
| 2018/0056027 A1 | 3/2018 | Peeters et al. | |
| 2018/0235041 A1* | 8/2018 | Trouwborst | H05B 45/20 |
| 2020/0303598 A1* | 9/2020 | Kim | H05B 45/20 |

FOREIGN PATENT DOCUMENTS

| | | |
|---|---|---|
| WO | 2017025613 A1 | 2/2017 |
| WO | 2017131713 A1 | 8/2017 |
| WO | 2017131714 A1 | 8/2017 |
| WO | 2017131715 A1 | 8/2017 |
| WO | 2018130403 A1 | 7/2018 |

* cited by examiner

US 11,330,686 B2

CYAN ENRICHED WHITE LIGHT

CROSS-REFERENCE TO PRIOR APPLICATIONS

This application is the U.S. National Phase application under 35 U.S.C. § 371 of International Application No. PCT/EP2019/072674, filed on Aug. 26, 2019, which claims the benefit of European Patent Application No. 18191993.7, filed on Aug. 31, 2018. These applications are hereby incorporated by reference herein.

FIELD OF THE INVENTION

The invention relates to a light generating device and a lighting system comprising such light generating device.

BACKGROUND OF THE INVENTION

Solid state light emitting devices including adjustable melatonin suppressing effects are known in the art. U.S. Pat. No. 9,039,746, for instance, describes a solid state light emitting device include multiple LED components providing adjustable melatonin suppression effects. Multiple LED components may be operated simultaneously according to different operating modes according to which their combined output provides the same or similar chromaticity, but provides melatonin suppressing effects that differ by at least a predetermined threshold amount between the different operating modes. Switching between operating modes may be triggered by user input elements, timers/clocks, or sensors (e.g., photo sensors). Chromaticity of combined output of multiple LED components may also be adjusted, together with providing adjustable melatonin suppression effects at each selected combined output chromaticity.

WO2016146688 describes a three-channel lighting apparatus with the option to support the human circadian rhythm. By choosing especially the blue LED and green phosphor, the range of biological activity that can be changed is optimized. By adjustment of the LED spectra a bigger range in melanopsin effectiveness factor, at the same CCT range (from daylight like CCT down to dimmed halogen), can be obtained.

U.S. Pat. No. 9,039,746 describes solid state light emitting devices which include multiple LED components providing adjustable melatonin suppression effects. Multiple LED components may be operated simultaneously according to different operating modes according to which their combined output provides the same or similar chromaticity, but provides melatonin suppressing effects that differ by at least a predetermined threshold amount between the different operating modes. Switching between operating modes may be triggered by user input elements, timers/clocks, or sensors (e.g., photosensors). Chromaticity of combined output of multiple LED components may also be adjusted, together with providing adjustable melatonin suppression effects at each selected combined output chromaticity.

WO2017025613 describes a lighting device comprising a first light source and a second light source, a control system configured to control the first light source and the second light source, wherein the first light source is configured to provide first light source light having a correlated color temperature (CCT) of at maximum 3000 K and a color rendering index of at least 75, and wherein the second light source is configured to provide second light source light having a dominant wavelength selected from the range of (575-780) nm and having a color rendering index of at maximum.

WO2018130403 describes a lighting system comprising a lighting device configured to provide light, wherein one or more lighting properties, including the spectral power distribution, of the light are controllable, wherein the lighting system further comprises a control system adapted to provide at least a controlling mode which comprises maintaining a predetermined melanopic flux value of the light while allowing another lighting property of the light to be changed from a first lighting property value to a second lighting property value.

US2004156192 describes a computing device. The computing device includes a housing having an illuminable portion. The computing device also includes a light device disposed inside the housing. The light device is configured to illuminate the illuminable portion.

SUMMARY OF THE INVENTION

Critical to our sleep/wake cycle is melatonin, a hormone that promotes sleep during night time. Melatonin is a sleep supportive hormone that we only produce around (and during) our usual bedtime. Light exposure during the evening and at night suppresses the natural production of melatonin. When the spectrum of the light is shifted towards lower CCT and intensity levels (like during dawn and dusk), this reduces melatonin suppression and makes the light less disruptive for sleep. During day time, natural daylight with high correlated color temperature (CCT, herein also indicated as "color temperature") and intensity energizes people making them awake and alert. Current high performance LED based lighting apparatus with tunable CCT are able to mimic different phases of daylight, i.e., changes in spectral power distribution and variations in CCT, to a certain extent.

Next to the commonly known cones and rods, the human eye has melanopsin containing photoreceptors, affecting circadian entrainment and melatonin secretion, which are sensitive in a specific wavelength range. The relative spectral sensitivity for the classic receptors (rods and cones) and for the melanopic receptors are provided in FIG. 8 (see also R. J. Lucas, et al., Measuring and using light in the melanopsin age, Trends in Neurosciences, Vol. 37, No. 1, January 2014, pp. 1-9; http://www.sciencedirect.com/science/article/pii/S0166223613001975, the report "CIE TN 003:2015: Report on the First International Workshop on Circadian and Neurophysiological Photometry, 2013" at http://cie.co.at/index.php?i_ca_id=978 (with a link to an excel toolbox http://files.cie.co.at/784_TN003_Toolbox.xls). If the spectral power in the melanopic wavelength range is absent or low, the light exposure will be less suppressive for the melatonin hormone production thus enabling faster sleep onset and more consolidated sleep. If the spectral power in the melanopic range is increased, a light exposure will result in stronger melatonin suppression. In general a light exposure can be said to be more biologically active and more alerting when the power in the melanopic range (and the ability to suppress melatonin at night) is increased. The effectiveness of a given light spectrum in suppressing melatonin production can be expressed in terms of the melanopsin effectiveness factor (MEF). This factor is calculated by multiplying the spectral power distribution of the light emitted by a lighting system (SPD($\lambda$)) with the melanopic sensitivity function (m($\lambda$)) divided by the product of SPD($\lambda$)

and the photopic sensitivity (V(λ)), normalized by the areas under the curves of m(λ) and V(λ), see equation 1 (and see also FIG. 1).

$$MEF = \left( \frac{\int_\lambda V(\lambda)d\lambda}{\int_\lambda m(\lambda)d\lambda} \right) \cdot \left( \frac{\int_\lambda SPD(\lambda)m(\lambda)d\lambda}{\int_\lambda SPD(\lambda)V(\lambda)d\lambda} \right) \quad \text{(eq. 1)}$$

This can be simplified to $$MEF = 1.22 \left( \frac{\int_\lambda SPD(\lambda)m(\lambda)d\lambda}{\int_\lambda SPD(\lambda)V(\lambda)d\lambda} \right) \quad \text{(eq. 2)}$$

as $$MEF = 1.22 \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3)}$$

Hence, the above indicated summations are over the visible range of 380-780 nm. By definition, the MEF for an equi-energy light source $MEF_{EE}$ equals 1. Especially, an equi-energy light source has SPD(λ)=constant (for example 1) for all (visible) wavelengths.

The maximum sensitivity of this sensor in the human eye (intrinsically Photosensitive Retinal Ganglion Cells or iPRGCs) is around 490 nm. Stimulation of the iPRGCs during daytime (or the absence of stimulation in the evening) is important to control the circadian rhythm (entrainment to the 24 hours cycle).

The melanopic efficiency of a light spectrum can be calculated using the MDEF (Melanopic D65 Efficiency Factor) (sometimes also indicated as MDER, i.e. Melanopic Daylight Efficacy Ratio). In such instance, instead of an equal energy light source, a D65 source, i.e. CIE Standard Illuminant D65, which is a commonly used standard illuminant defined by the International Commission on Illumination (CIE). MDEF can be defined as the illuminance in lux of a D65 source needed to generate the same stimulation of the iPRGCs per lux of the test source (or test system). The MDEF value of a D65 source is approximately 0.906* the MEF value. Instead of the MDEF value, also the MELR value may be applied. The term MELR refers to melanopic efficacy of luminous radiation (see also below).

The MDEF of a set of spectra of commercially available light sources was calculated and plotted as a function of v' (blue content of a spectrum). Results are displayed in FIG. 7. With increasing CCT (lower v') MDEF increases. At a given v' still a range of MDEFs is available; e.g. at 4000K (v'=0.502) MDEF varies between 0.5 and 0.75. The biological effect of lighting is the product of Illumination (Lux at the eye)×MDEF×(Exposure time). Next to that, also the time of exposure (morning/evening) determines the effect on people. In normal indoor lighting conditions, the stimulation of the iPRGCs during daytime is too low (e.g. 500 lux in offices, 4000K, MDEF ~0.6). Hence, there is a need to provide adapted or adaptable (indoor) lighting.

Increasing the iPRGCs stimulation can be done by increasing the intensity, or by increasing the CCT (blue enriched). Both options have limitations due to unwanted side effects, such as increasing glare. Further, in some parts of the world high CCTs are disliked.

Adding blue/green light to a white emitter, such as a white emitter having a correlated color temperature above about 2700 K, especially above about 3000 K, appears to provide white light that give a greenish appearance, even when the color point is on the BBL (black body locus). This is also undesired.

Hence, it is an aspect of the invention to provide an alternative light generating device, which preferably further at least partly obviates one or more of above-described drawbacks. The present invention may have as object to overcome or ameliorate at least one of the disadvantages of the prior art, or to provide a useful alternative.

In a first aspect, the invention provides a light generating device configured to generate (in a first control mode) device light (or "lighting device light"). In specific embodiments, the light generating device comprises (i) a first source of first light, and (ii) a second source of second light. Especially, the second source is different from the first source. Further, especially (in the first control mode) the second light is different from the first light.

In specific embodiments, the light generating device is configured to generate the first light and the second light. In specific embodiments, the first source is arranged to generate the first light and/or the second source is arranged to generate the second light.

Especially, the second light comprises cyan-like light having a wavelength selected from the range of 470-520 nm. In specific embodiments, the second light may have a dominant wavelength selected from the range of 470-510 nm, such as selected from the range of 474-500 nm, even more especially selected from the range of 474-490 nm, like 475-490 nm, such as 475-488 nm.

Herein, the phrase "having a wavelength selected from the range", and similar phrases, may also refer to "having one or more wavelengths selected from the range".

Further, in specific embodiments the device light comprises the first light and the second light. Especially, the lighting device light (in the first control mode) essentially consists of the first light and the second light. Yet, in embodiments in the first control mode the first light is white light or cyan-depleted white light. Further, especially in the first control mode the device light is white light. Especially, the first light and the device light having different spectral distributions.

In embodiments, the first light is white light, whereas the device light comprises the first light enriched with the second light, with (at least) the latter comprising cyan-like light.

In yet other embodiments, the first light is cyan-depleted white light. Especially, the term cyan-depleted white refers to light having a color point in the range of 15-30 SDCM below the black body locus, such as in the range of 15-25 SDCM below the BBL. Especially, the color point is >15 SDCM below the BBL. Further, especially the term "cyan-depleted white light" may be attributed (visible) light having a correlated color temperature of at maximum 4000 K. Hence, this light may be considered whitish, or even colored light, as it has a color point substantially below the BBL. When the first light is cyan-depleted white light, the color temperature of at maximum 4000 K at the BBL may be selected, and those color point that are obtained at 15-30 SDCM below the BBL having a color temperature of at maximum 4000 K, such as at maximum 3500 K, are herein especially defined as cyan-depleted white light. Hence, in embodiments (in the first control mode) the first light may be cyan-depleted white light having a correlated color temperature of at maximum 3500 K and having a color point in the range of 15-30 SDCM, such as 15-25 SDCM below the black body locus. In specific embodiments, the first light may have a correlated color temperature of at minimum 2200 K, especially at least 2300 K, such as at least 2500 K, like at least 2700 K.

Hence, especially the invention provides a light generating device configured to generate in a first control mode device light, wherein the light generating device comprises (i) a first source of first light, and (ii) a second source of second light, different from the first light, wherein the second light comprises cyan-like light having a wavelength selected from the range of 470-520 nm, especially at least in the range of 490-520 nm, wherein the device light comprises the first light and the second light, and wherein in the first control mode the first light is white light or cyan-depleted white light, and wherein the device light is white light.

In yet a further aspect, the invention provides a light generating device comprising a first light source and a second light source, wherein in embodiments the first light source is configured to generate blue first light source light, and wherein in embodiments the second light source is configured to generate cyan-like second light source light. Especially, the second light source light has one or more wavelengths selected from the range of 470-520 nm. The light generating device further comprises the first luminescent material configured to convert part of one or more of the first light source light and the second light source light into first luminescent material light. Optionally, the light generating device may further comprise a second luminescent material, configured to convert part of one or more of the first light source light and the second light source light into second luminescent material light. Especially, the first light source and the second light source are configured upstream of the first luminescent material and the optional second luminescent material. Especially, in the first control mode the device light is white light comprising the first light source light, the second light source light, the first luminescent material light and the optional second luminescent material light. Especially, in embodiments the device light has a color rendering index of at least 80. In specific embodiments, the first luminescent material light has one or more wavelengths in the yellow wavelength range, and the second luminescent material light has one or more wavelength in the red wavelength range. Herein, the term "second luminescent material" may also refer to two or more different second luminescent materials. The second luminescent material is different from the first luminescent material; the spectral power distribution of the first luminescent material and the second luminescent material are different (see also below). In embodiments, the first light source and the second light source may be configured in a single LED string. In (other) embodiments, the (blue) first light source and the (cyan) second light source may be controllable, which allows control of the spectral power distribution of the device light. In this way e.g. CCT and/or MDEF may be controllable possible. The light sources are especially solid state light sources (see also below). In embodiments, the lighting device comprises a package wherein the solid state light sources are at least partly embedded in a luminescent material comprising material. The luminescent material comprising material may be a combination of the two or more luminescent material. In embodiments, the two or more luminescent material may be comprises in a light transmissive material, like silicone. Other materials may also be possible. Especially, at least one luminescent material is configured to provide yellow luminescent material light, especially having a dominant wavelength in the green-yellow, and at least one luminescent material is configured to generate red luminescent material light, especially having a dominant wavelength in the red. The first luminescent material may e.g. be a cerium comprising lutetium comprising garnet and/or a cerium comprising gallium comprising garnet (see also below). The second luminescent material may be an europium comprising $MAlSiN_3$ nitride (see also below). Further, the first light source may have a dominant wavelength selected from the range of 445-455 nm, such as selected from the range of about 448-452 nm. The second light source may have a dominant wavelength selected from the range of 470-480 nm, like selected from the range of about 473-482 nm. For instance, the respective dominant wavelengths may be about 450 and 475 nm.

Such light generating device(s) may provide device light with a high correlated color temperature, such as at least about 3500 K, like at least about 4000 K, and a reasonable to relatively high color rendition (CRI), such as over 80. Further, such light may provide a relative strong stimulation of the ipRGCs. In general, in embodiments the color temperature of the device light is higher than the color temperature of the first light.

The term white light herein, is known to the person skilled in the art. It especially relates to light having a correlated color temperature (CCT) between about 2000 and 20000 K, especially 2700-20000 K, for general lighting especially in the range of about 2700 K and 6500 K, and for backlighting purposes especially in the range of about 7000 K and 20000 K, and especially within about 15 SDCM (standard deviation of color matching) from the BBL (black body locus), especially within about 10 SDCM from the BBL (even more especially within about 5 SDCM from the BBL). Hence, in embodiments the device light (in the first control mode) may have a color point within 15 SDCM from the black body locus. In specific embodiments, however, the device light is at least 3 SDCM below the BBL. Therefore, in specific embodiments, however, the device light is at least 3 SDCM below the BBL.

The relatively high color rendition may especially be obtained when the color point of the device light is chosen (slightly) below the black body locus or Planckian locus (BBL), such as at least about 3 SDCM below the BBL (see further also below).

Hence, as indicated above the invention provides a light generating device. Instead of the term "light generation device" also the term "lighting device" may be applied. The light generation device is especially configured to generate visible light. The light generation device can be used indoors and outdoors, but may especially be used indoors. The light generating device may be part of or may be applied in e.g. office lighting systems, household application systems, shop lighting systems, home lighting systems, accent lighting systems, spot lighting systems, theater lighting systems, fiber-optics application systems, projection systems, self-lit display systems, pixelated display systems, segmented display systems, warning sign systems, medical lighting application systems, indicator sign systems, decorative lighting systems, portable systems, automotive applications, (outdoor) road lighting systems, urban lighting systems, green house lighting systems, horticulture lighting, or LCD backlighting. Embodiments of lighting systems in general, comprising such light generation device, are further discussed below.

As indicated above, the light generating device is configured to generate (in a first control mode) device light. The system, or apparatus, or device may execute an action in a "mode" or "operation mode" or "mode of operation" or "control mode". Likewise, in a method an action or stage, or step may be executed in a "mode" or "operation mode" or "mode of operation" or "control mode" or "controlling mode". The term "mode" may also be indicated as "controlling mode". This does not exclude that the system, or apparatus, or device may also be adapted for providing another controlling mode, or a plurality of other controlling modes. Likewise, this may not exclude that before executing the mode and/or after executing the mode one or more other modes may be executed.

The term "control mode" may also refer to a plurality of different control modes. Likewise, the term "first control mode" may also refer to a plurality of different first control modes. For instance, for each of the first control modes one or more of the conditions concerning (i) MDEF and/or MELR, (ii) color point (at least 3 SDCM) below the BBL, (iii) color temperature, and optionally other conditions defined herein, may apply.

Instead of the phrase "in the first control mode" also the phrase during the first control mode" may be applied.

However, in embodiments a control system may be available, that is adapted to provide at least the controlling mode. Would other modes be available, the choice of such modes may especially be executed via a user interface, though other options, like executing a mode in dependence of a sensor signal or a (time) scheme, may also be possible. This will further be elucidated below.

The operation mode may in embodiments also refer to a system, or apparatus, or device, that can only operate in a single operation mode (i.e. "on", without further tunability). Hence, in specific embodiments the first control mode is the only control mode (off mode is not considered a control mode). In such embodiments, the device light may have essentially fixed optical properties, such as spectral distribution, color point, color temperature, etc. In yet other embodiments, the spectral properties of the device light are controllable, i.e. that the light generating device may be controllable and allow more than a single control mode.

A system comprising the light generating device is further described below.

When below the "device light" is discussed in relation to the light generation device, in general it will be referred to the device light that is generated in the first control mode. Hence, especially the device light (in the first control mode) is white device light. The herein described device light may be provided via different embodiments, which will be elucidated further below.

In specific embodiments, the light generating device comprises (i) a first source of first light, and (ii) a second source of second light. The source of light provides the respective light during operation of the device in the first control mode.

With respect to the term "source of light" it is herein indicated that in embodiments the light generation device especially comprises at least two sources of light. In embodiments, two or more of the at least two sources of light may be comprised in the same (LED) package. Even a combination of two luminescent materials may qualify as two sources of light. However, e.g. a tungsten lamp which has a relative broad spectral distribution comprising white light, which may also include a cyan hue, is considered a single source of light. Hence, e.g. a blue LED with a yellow phosphor (or "luminescent material") may be considered as two sources of light, as such LED will provide white light based on a source of blue light and another source of yellow light. Hence, especially, the second source is different from the first light. The first light and the second light may thus be considered to originate from different species, such as from different LED dies, or from a LED die and from a luminescent material, or from different luminescent materials, etc.

The term "first source of light" may also refer to a plurality of (different) first sources of light, which may together provide the first light. Likewise, the term "second source of light" may also refer to a plurality of (different) second sources of light, which may together provide the second light. The term "spectral distribution" especially refers to the spectral distribution of the light in the visible, i.e. in the visible wavelength range.

The terms "violet light" or "violet emission" especially relates to light having a wavelength in the range of about 380-440 nm. The terms "blue light" or "blue emission" especially relates to light having a wavelength in the range of about 440-495 nm (including some violet and cyan hues).

More especially, the term blue light herein refers to light having a peak wavelength selected from the range of 440-470 nm, especially selected from the wavelength range of 440-460 nm. Further, especially herein when a blue light source is applied, such as a solid state light source emitting in the blue, especially a solid state light source wherein the die emits such light and no luminescent material is involved, at least 50%, such as especially at least 60%, even more especially at least 70%, like yet even more especially at least about 75%, such as at least about 80%, of the total power of the light source light in the visible range is in the range of 440-470 nm, especially selected from the wavelength range of 440-460 nm.

The terms "green light" or "green emission" especially relate to light having a wavelength in the range of about 495-570 nm. The terms "yellow light" or "yellow emission" especially relate to light having a wavelength in the range of about 570-590 nm. The terms "orange light" or "orange emission" especially relate to light having a wavelength in the range of about 590-620 nm. The terms "red light" or "red emission" especially relate to light having a wavelength in the range of about 620-780 nm. The term "pink light" or "pink emission" refers to light having a blue and a red component. The terms "visible", "visible light" or "visible emission" refer to light having a wavelength in the range of about 380-780 nm.

In embodiments, the second light comprises cyan-like light. In embodiments, the second light may (essentially) consist of cyan-like light. In such embodiments, the spectral distribution of the second light has at least 50%, even more especially at least 60%, even more especially at least 70%, such as at least 75%, like yet even more especially at least 80% of the total power in the cyan-like spectral region, i.e. in the wavelength range of 470-520 nm (relative to the total power in the visible range of 380-780 nm), even more especially at least 90%, such as at least 95%.

Herein, light having a wavelength selected from the wavelength range of 470-520 nm is indicated as cyan-like light. Further, light having a wavelength selected from the range of 490-520 nm is indicated as cyan light. Especially, in embodiments light having a spectral distribution with a centroid wavelength in the range of 495-510 nm is herein indicated as cyan light.

In embodiments, the spectral distribution of the second light has at least 50%, even more especially at least 60%, even more especially at least 70%, like yet even more especially at least 80%, relative to the total power in the visible range (of the second light), in the cyan spectral region, i.e. in the wavelength range of 490-520 nm.

Further, in specific embodiments the device light—in the first control mode—comprises the first light and the second light. In yet further specific embodiments, the device light (in the first control mode) essentially consists of the first light and the second light. In such embodiments, the spectral distribution of the device light consists of the first light and the second light for at least 90%, even more especially at least 95% of the total power in the visible spectral region (i.e. visible wavelength range).

Further, in specific embodiments the device light—in the first control mode—comprises the first light and the second light and optional further light (of one or more further sources of light). In yet further specific embodiments, the device light (in the first control mode) essentially consists of the first light, the second light, and the further light. In such embodiments, the spectral distribution of the device light consists of the first light, the second light, and the further light, for at least 90%, even more especially at least 95% of the total power in the visible spectral region (i.e. visible wavelength range).

Further, in specific embodiments, in the first control mode at least 5%, such as in the range of 5-35% of the total power within the visible wavelength range of the device light is cyan-like light, especially at least 15%, such in the range of 15-30%, like in the range of 20-30%, or even above about 22%. In embodiments, a substantial part thereof may be comprised by the second light.

As indicated above, in embodiments in the first control mode the first light is white light and also the device light is white light. Especially, the first light and the device light (thus) have different spectral distributions. The first light is white light, whereas the device light comprises the first (white) light enriched with the second light, with (at least) the latter comprising cyan-like light. Hence, in the first control mode the device especially provides cyan enriched white light.

The light generating device includes in specific embodiments a first source of light and a second source of light. In embodiments, this does not exclude the availability of one or more further sources of light. Such one or more further sources of light and the (one or more (different) types of) light generated thereby, respectively, are herein further indicated as "further sources of light". Hence, the device light generated by the light generating device comprises—in the first mode—the light of the first source of light, the light of the second source of light, and when further sources of light are available and one or more of these generate also further light during the first mode, then also the further light of the optional one or more further sources of light.

The phrase "further sources of light" may refer to one or more (optionally) additional sources of light. When two or more further sources of light are available, in embodiments two or more of these may have different spectral distributions. The term "further source of light" may (also) refer to a plurality of (different) further sources of light, which may together provide the further light.

As also indicated above, it seems desirable that the color point of the white device light is below the BBL. Hence, in specific embodiments the first source, the second source, optional further sources of further light, and the first control mode, are chosen to obtain a color point of the device light at at least 3 SDCM below the black body locus, such as in the range of 3-5 SDCM, or even 3-10 SDCM below the black body locus, such as at least 5 SDCM.

In specific embodiments, which may provide an even higher CRI, the color point of the device light is (chosen) at at least 5 SDCM below the black body locus (in the first control mode). Hence, in further specific embodiments the first source, the second source, optional further sources of further light, and the first control mode, are chosen to obtain a color point of the device light in the range of 5-10 SDCM below the black body locus.

With the present invention, it appears that device light can be generated with a high MEF or high MDEF, higher than essentially any commercial light source known, especially when the CCT is chosen to be at least 2000 K, such as at least 2500 K, like at least 2700 K, such as even about 3000 K, like at least 3500 K, or even at least about 4000 K. It is even possible to create at some instances MEF or MDEF values above the respective values D65, especially when the CCT is equal to or above about 4500 K, such as equal to or above about 5000 K. Nevertheless, the CRI may be relatively high and the greenish appearance may essentially be absent. Therefore, with the present invention unique lighting can be provided in a relatively simple way.

In specific embodiments, the light generating device is configured to provide in the first control mode the device light having a MDEF value of $\geq 5.43\text{-}9.31*v'$, wherein the MDEF is defined as:

$$MDEF = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3a)}$$

wherein $SPD(\lambda)$ is the spectral power distribution of the light emitted by a light generating device, $m(\lambda)$ is the melanopic sensitivity function, the $V(\lambda)$ is the photopic sensitivity.

Hence, in an aspect the invention provides a light generating device configured to generate in a first control mode device light, wherein the light generating device comprises (i) a first source of first light, and (ii) a second source of second light, different from the first light, wherein the device light comprises the first light and the second light, and wherein in the first control mode the device light is white light, and wherein the light generating device is configured to provide in the first control mode the device light having a MDEF value of $\geq 5.43\text{-}9.31*v'$, wherein the MDEF is defined as:

$$MDEF = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3a)}$$

wherein $SPD(\lambda)$ is the spectral power distribution of the light emitted by a light generating device, $m(\lambda)$ is the melanopic sensitivity function, the $V(\lambda)$ is the photopic sensitivity.

Herein, u' and v' especially refer to the color coordinates in the CIELUV color space (1976). In embodiments, v' may be selected from the range of 0.44-0.57, such as selected from the range of 0.45-0.56, like especially selected from the range of 0.46-0.55. In embodiments, v' may be at least 0.49, such as at least 0.50, like at least 0.51. In embodiments, u' may be selected from the range of 0.18-0.30. As can be derived from the above, u' and v' are especially selected to provide white light within 15 SDCM from the BBL.

The invention provides (in embodiments) a light generating device (100) comprising a first light source and a second light source, wherein the first light source (110) is configured to generate blue first light source light (111), wherein the second light source (120) is configured to generate cyan-like second light source light (121) having one or more wavelengths selected from the range of 470-520 nm, wherein the light generating device (100) further comprises the first luminescent material (310), configured to convert part of one or more of the first light source light (111) and the second light source light (121) into first luminescent material light (311), and optionally a second luminescent material (320), configured to convert part of one or more of the first light source light (111) and the second light source light (121) into second luminescent material light (321), wherein the first light source (110) and the second light source (120) are configured upstream of the first luminescent material (310) and the optional second luminescent material (320), wherein in the first control mode the device light (101) is white light comprising the first light source light (111), the second light source light (121), the first luminescent material light (311) and the optional second luminescent material light (321), and wherein the light generating device is configured to provide in the first control mode the device light having a MDEF value of ≥5.43-9.31*v'.

As indicated above, in specific embodiments the second light (in the first control mode) comprises cyan-like light having a wavelength selected from the range of 470-520 nm. Further, as indicated above, in the first control mode the first light is white light, or cyan-depleted white light.

Hence, in yet a further aspect the invention provides a light generating device configured to generate in a first control mode device light, wherein the light generating device comprises (i) a first source of first light, and (ii) a second source of second light, different from the first light, wherein the second light comprises cyan-like light having a wavelength selected from the range of 470-520 nm, wherein the device light comprises the first light and the second light, and wherein in the first control mode the first light is white light, or cyan-depleted white light, and the device light is white light, and wherein the light generating device is configured to provide in the first control mode the device light having a MDEF value of ≥5.43-9.31*v', wherein the MDEF is defined as:

$$MDEF = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3a)}$$

wherein SPD(λ) is the spectral power distribution of the light emitted by a light generating device, m(λ) is the melanopic sensitivity function, the V(λ) is the photopic sensitivity.

Hence, especially the first source, the second source, optional further sources of further light, and the first control mode, are chosen to obtain a MDEF value of the device light of ≥5.43-9.31*v', such as ≥5.45-9.31*v', or even 5.46-9.31*v'.

In specific embodiments, the light generating device comprises (i) a first light source configured to generate first light source light comprising the first light, and (ii) a first luminescent material configured to convert part of the first light source light into the first luminescent material light, wherein the second light comprises at least part of the first luminescent material light. The first light source light may comprise the first light and in addition to this light, the light may be relatively rich in e.g. blue light. The first luminescent material may convert part of the blue light into first luminescent material light, whereby the device light may comprise or may essentially consist of the first light and the second light. In further specific embodiments, the device light may comprise or may essentially consist of the first light and the luminescent material light. As indicated herein, the first light may be essentially white light and the second light may substantially comprise cyan-like light.

For instance, in embodiments the light generating device may comprise a (blue enriched) white light emitting solid state light source in combination with a luminescent material, that may in embodiments be contained in a resin (together with e.g. one or more other luminescent materials), or which may be applied as coating on a support, such as the resin, etc.

When a luminescent material is applied herein, the luminescent material is especially configured downstream of a light source, such as in the above embodiment the white light emitting solid state light source. The light source may thus in embodiments be configured upstream of the luminescent material, with the luminescent material being configured to convert at least part of the light source light. The terms "upstream" and "downstream" relate to an arrangement of items or features relative to the propagation of the light from a light generating means (here the especially the light source), wherein relative to a first position within a beam of light from the light generating means, a second position in the beam of light closer to the light generating means is "upstream", and a third position within the beam of light further away from the light generating means is "downstream".

Hence, in specific embodiments the light generating device comprises a first light source configured to generate first light source light, a first luminescent material configured to convert part of the first light source light into the first luminescent material light, wherein the second light comprises at least part of the first luminescent material light, a second luminescent material configured to convert part of the first light source light into second luminescent material light, and optionally one or more further luminescent materials configured to convert part of first light source light into further luminescent material light, and wherein the device light comprises the first light source light, the first luminescent material light, the second luminescent material light, and the optional further luminescent material light.

For instance, the second light may comprise first luminescent material light that has a (substantial) intensity in the cyan-like part of the visible spectrum, especially at least partly in the cyan spectral part of the visible spectrum. Hence, in embodiments the second source of light provides—in the first control mode—first luminescent material light that has a (substantial) intensity in the cyan-like part of the visible spectrum.

Further, especially the first luminescent material light may have a spectral distribution with at least 40%, even more especially at least 50%, such as at least 60% of the total power in the cyan-like spectral region, especially in the cyan region, relative to the total power in the visible wavelength range.

Hence, the first luminescent material can be seen a second source of light. Hence, in embodiments the second light comprises at least part of the first luminescent material light.

Especially, in (such) embodiments the first light source light may comprise blue light.

The second luminescent material may especially be configured to convert (also) part of the first light source light into green and/or yellow light comprising second luminescent material light. When the second luminescent material light is essentially green, then a further source of light may be useful, such as in embodiments a further luminescent material. When the second luminescent material light is essentially yellow, then it may still be desirable to add some red luminescent material light. Hence, one or more further luminescent materials may be applied.

Hence, in embodiments—in the first control mode—the first source of light (or in fact first sources of light) may provide white light (or cyan-depleted white light), based on the blue light source light, the second luminescent material light and the optional further luminescent material light.

Therefore, in embodiments the device light comprises—in the first control mode—the (blue) first light source light, the first luminescent material light, the second luminescent material light, and the optional further luminescent material light.

Especially, the light generating device comprises in specific further embodiments a luminescent element comprising the first luminescent material, the second luminescent material, and the optional one or more further luminescent materials. The term "luminescent element" may in embodiments refer to a resin (further) comprising e.g. one or more (different) luminescent materials. The term "luminescent element" may in embodiments refer to a coating (further) comprising e.g. one or more (different) luminescent materials on a support, such as the resin, etc. The term "luminescent element" may in embodiments refer to multi-layer, wherein one or more of the layers of the multi-layers comprise one or more (different) luminescent materials. The term "luminescent element" may in embodiments refer to a luminescent body, such as a self-supporting body, like e.g. a ceramic body, such as a ceramic slab.

Especially, the luminescent element may be configured downstream of the first light source that is configured to generate (in above-mentioned embodiment(s)) first light source light comprising blue light.

In embodiments, e.g. a UV emitting first light source may be applied (instead of or in addition to a blue emitting first light source). Therefore, in embodiments the light generating device comprises a first light source configured to generate first light source light, a first luminescent material configured to convert part of the first light source light into first luminescent material light, a second luminescent material configured to convert part of the first light source light into second luminescent material light, and one or more further luminescent materials configured to generate further luminescent material light, wherein the second light comprises at least part of the first luminescent material light, wherein the device light comprises the first luminescent material light, the second luminescent material light and the further luminescent material light.

Hence, especially in (such) embodiments the first light source light may comprise UV light. More especially, the spectral distribution in the UV and visible of the first light source light may consist for at least 90% of the total power, even more especially at least 95% of light in the UV region, which is essentially in the 100-380 nm wavelength region, such as 250-380 nm.

Further, especially the first luminescent material light may have a spectral distribution with at least 40%, even more especially at least 50%, such as at least 60% of the total power in the cyan-like spectral region. Hence, the first luminescent material can be seen a second source of light. Therefore, in embodiments the second light comprises at least part of the first luminescent material light.

The second luminescent material may especially be configured to convert part of the first light source light into blue light comprising second luminescent material light (i.e. second luminescent material light that comprises, or may essentially consist of, blue light).

The one or more further luminescent materials configured to generate further luminescent material light. The further luminescent material light may comprise yellow light, or green and red light, or yellow and red light. Similar to the above, when the further luminescent material light comprises green light, it will also comprise red light. When the further luminescent material light is essentially yellow, then it may still be desirable to add some red light (e.g. from another further luminescent material).

Hence, in embodiments—in the first control mode—the first source of light (or in fact first sources of light) may provide white light (or cyan-depleted white light), based on the blue second luminescent material light, the further luminescent material light (comprising yellow light, or green and red light, or yellow and red light), and the second source of light provides the second light comprising at least part of the first luminescent material light.

Therefore, the device light comprises the first luminescent material light, the second luminescent material light, and the further luminescent material light.

Also in the above embodiment(s), the light generating device may comprise in specific further embodiments a luminescent element comprising the first luminescent material, the second luminescent material, and the one or more further luminescent materials.

Especially, when a single light source comprising a luminescent material is applied, wherein the luminescent material is configured to generate the cyan-like light, then the spectral distribution of the device light may be a combination of the cyan-depleted white light and the cyan-like light. In other words, would the contribution of the cyan-like light of the luminescent material be subtracted from the device light, cyan-depleted white light may remain. This may also apply when the luminescent material is remote from a solid state light source, but the solid state light source together with the luminescent material provides the device light.

Hence, in embodiments the device light may comprise, or essentially consist of, first light that is essentially white light combined with cyan-like light. In other embodiments the device light may comprise, or essentially consist of, first light that is essentially cyan-depleted white light combined with cyan-like light. Hence, in specific embodiments the first light comprises white light and the second light comprises cyan-like light, such as cyan light. In other specific embodiments the first light comprises cyan depleted white light and the second light comprises cyan-like light, such as cyan light. In embodiments, one or more sources of light, such as the first source of light, the second source of light and optionally further sources of light, may be configured to the device light.

In yet further embodiments, the source of cyan-like light and the source of white light may be different sources in the sense of e.g. independently driven, independently controllable, separate solid state light sources, etc. etc. Hence, when e.g. using a luminescent material that can be used as source of second light, such luminescent material may be excited with light that is generated by or in the same source of light that generates white light, or may be excited with a separate light source. In the former variant(s) control of the relative contributions of the first light and second light may essentially not be possible; in the latter variant(s) control of the relative contributions of the first light and second light may be possible (though fixed embodiments are herein also included).

In embodiments, the light generating device may comprise (i) a first light source configured to generate first light source light comprising the first light, (ii) a second light source configured to generate second light source light, and (iii) a first luminescent material configured to convert at least part of the second light source light into first luminescent material light, wherein the second light comprises at least part of the first luminescent material light and optionally (unconverted) second light source light.

In embodiments, such first light source may be a light source that can only be switched on or off, i.e. not tunable. In an alternative embodiment, such first light source may be controllable. The term "first light source" may also refer to a plurality of (different) light sources, which may together provide the first light source light (in the first control mode). Especially, the first light source comprises one or more solid state light sources.

Alternatively or additionally, in embodiments such second light source may be a light source that can only be switched on or off, i.e. not tunable. In an alternative embodiment, such second light source may be controllable. The term "second light source" may also refer to a plurality of (different) light sources, which may together provide the second light source light (in the first control mode). Especially, the second light source comprises one or more solid state light sources.

The availability of a first light source and a second light source does not exclude the availability of other light sources, different from the first light source and the second light source (where "different" especially refers to a spectral power distribution of the light source light of such other light source compared to the spectral power distributions of the first light source light and second light source light).

In specific embodiments, the first light source may comprises a first solid state light source, the second light source may comprise a second solid state light source, wherein the first solid state light source and the second solid state light source are configured in series in a LED string. Hence, in embodiments the first light source and the second light source may be configured in series in a LED string. However, they may also be configured in different strings. Further, a plurality of different strings may be controlled by a control system, in embodiments for controlling the spectral power distribution of the lighting device light.

Therefore, in specific embodiments one or more the first light source and the second light source are controllable, especially both (see further also below). In other words, the first light source light and/or the second light source light may be controllable.

Especially, in embodiments the first light source light comprises the first light. In further specific embodiments, the first light source light essentially consists of the first light. Hence, especially the first light source light is white light (though may be cyan-depleted white light). Hence, the first source of light may comprise at least part of the first light source light. Especially, in these embodiments however, the first light source is essentially the source of first light.

Especially, in embodiments the second source of light comprises at least the first luminescent material light, which may comprise cyan-like light. Especially, the first luminescent material light may have a spectral distribution with at least 40%, even more especially at least 50%, such as at least 60% of the total power in the cyan-like spectral region. Optionally, especially when a blue light source is applied, the second source of light may comprise the first luminescent material light and optionally remaining light source light. In specific embodiments, the second source of light provides second light having a spectral distribution with at least 40%, even more especially at least 50%, such as at least 60% of the total power in the cyan-like spectral region, even more especially at least 70%, such as at least 80%. Hence, in embodiments the second light has a spectral distribution in the visible wavelength range wherein at least 40%, or even at least 80% of the total power is in the wavelength range of 470-520 nm.

In specific embodiments, wherein especially good results are obtained when using a first luminescent material that is configured to convert light source light into first luminescent material light comprising cyan-like light, the second light has a color point (u';v') defined by the CIE u'v' area (0.03; 0.22), (0.12;0.22), (0.03;0.55), and (0.12;0.55) in the CIE u'v' color space. In yet more specific embodiments, the second light has a color point (u';v') defined by the CIE u'v' area (0.03;0.29), (0.11;0.29), (0.03;0.43), and (0.11;0.43) in the CIE u'v' color space. Yet even better results in terms of CRI may be obtained when the second light has a color point (u';v') defined by the CIE u'v' area (0.04;0.32), (0.105;0.32), (0.04;0.395), and (0.105;0.395) in the CIE u'v' color space.

An example of a suitable luminescent material to provide cyan (comprising) luminescent material light is e.g. $ML_2O_2N_2:Eu^{2+}$. Hence, in embodiments the first luminescent material comprises $ML_2O_2N_2:Eu^{2+}$, wherein M is selected from the group consisting of Ca, Sr and Ba, and wherein L is selected from the group consisting of Si and Ge. Especially, in embodiments L at least comprises Si. More especially, L essentially consists of Si, such as at least 95% of all L comprises Si. The element M may comprise one or more of Ca, Sr, and Ba, such as Sr and Ba, like e.g. $(Sr,Ba)L_2O_2N_2:Eu^{2+}$. Especially, L at least comprises Ba. More especially, L essentially consists of Ba, such as at least 95% of all L comprises Ba, such as $BaSi_2O_2N_2:Eu^{2+}$. Up to about 5%, such as up to about 2%, like up to about 1% of M may consist of divalent Europium, such as in the range of 0.5-2%.

Alternatively or additionally, $M_4Z_{15}O_{25}:Eu^{2+}$ may be chosen, wherein M may comprise one or more of Ca, Sr, and Ba, such as Sr and Ba, especially at least one or more of Sr and Ba, even more especially at least Sr, and wherein Z is chosen from the group consisting of Al and Ga, especially at least Ga.

Especially, in embodiments Z at least comprises Al. More especially, Z essentially consists of Al, such as at least 95% of all Z comprises Al. The element M may comprise one or more of Ca, Sr, and Ba, such as Sr and Ba, like e.g. $(Sr,Ba)_4Z_{15}O_{25}:Eu^{2+}$. Especially, L at least comprises Sr. More especially, L essentially consists of Sr, such as at least 95% of all L comprises Sr, such as $Sr_4Al_{14}O_{25}:Eu$. Up to about 5%, such as up to about 2%, like up to about 1% of M may consist of divalent Europium, such as in the range of 0.5-2%.

Alternatively or additionally, $(Ba_9Lu_{(2-x)}Ce_xSi_6O_{24}$ with $0.01 \leq x \leq 0.05$) may be applied. Optionally, Ba may at least partly be replaced by one or more of Sr and Ca, especially Sr. Optionally, Lu may at least partly be replaced by one or more of Y, La and Gd, especially La and/or Gd.

For green, yellow, orange, and/or red emitting luminescent material, e.g. inorganic luminescent material with activators or active species may be applied. Relevant active species may e.g. $Eu^{2+}$ or $Ce^{3+}$. Other active species may be quantum dots. Yet other active species may be organic luminescent dyes.

In embodiments, luminescent materials may be selected from garnets and nitrides, especially doped with trivalent cerium or divalent europium, respectively. Embodiments of garnets especially include $A_3B_5O_{12}$ garnets, wherein A comprises at least yttrium or lutetium and wherein B comprises at least aluminum. Such garnets may be doped with cerium (Ce), with praseodymium (Pr) or a combination of cerium and praseodymium; especially however with Ce. Especially, B comprises aluminum (Al), however, B may also partly comprise gallium (Ga) and/or scandium (Sc) and/or indium (In), especially up to about 20% of Al, more especially up to about 10% of Al (i.e. the B ions essentially consist of 90 or more mole % of Al and 10 or less mole % of one or more of Ga, Sc and In); B may especially comprise up to about 10% gallium. In another variant, B and O may at least partly be replaced by Si and N. The element A may especially be selected from the group consisting of yttrium (Y), gadolinium (Gd), terbium (Tb) and lutetium (Lu). Further, Gd and/or Tb are especially only present up to an amount of about 20% of A. In a specific embodiment, the garnet luminescent material comprises $(Y_{1-x}Lu_x)_3B_5O_{12}$:Ce, wherein x is equal to or larger than 0 and equal to or smaller than 1.

The term ":Ce", indicates that part of the metal ions (i.e. in the garnets: part of the "A" ions) in the luminescent material is replaced by Ce. For instance, in the case of $(Y_{1-x}Lu_x)_3Al_5O_{12}$:Ce, part of Y and/or Lu is replaced by Ce. This is known to the person skilled in the art. Ce will replace A in general for not more than 10%; in general, the Ce concentration will be in the range of 0.1 to 4%, especially 0.1 to 2% (relative to A). Assuming 1% Ce and 10% Y, the full correct formula could be $(Y_{0.1}Lu_{0.89}Ce_{0.01})_3Al_5O_{12}$.

Ce in garnets is substantially or only in the trivalent state, as is known to the person skilled in the art.

Blue luminescent concentrators can be based on YSO ($Y_2SiO_5$:$Ce^{3+}$), or similar compounds, or BAM ($BaMgAl_{10}O_{17}$:$Eu^{2+}$), or similar compounds, especially configured as single crystal(s).

In embodiments, a red luminescent material may comprise one or more materials selected from the group consisting of (Ba,Sr,Ca)S:Eu, (Ba,Sr,Ca)AlSiN$_3$:Eu and (Ba,Sr,Ca)$_2$Si$_5$N$_8$:Eu. In these compounds, europium (Eu) is substantially or only divalent, and replaces one or more of the indicated divalent cations. In general, Eu will not be present in amounts larger than 10% of the cation; its presence will especially be in the range of about 0.5 to 10%, more especially in the range of about 0.5 to 5% relative to the cation(s) it replaces. The term ":Eu", indicates that part of the metal ions is replaced by Eu (in these examples by $Eu^{2+}$). For instance, assuming 2% Eu in CaAlSiN$_3$:Eu, the correct formula could be $(Ca_{0.98}Eu_{0.02})AlSiN_3$. Divalent europium will in general replace divalent cations, such as the above divalent alkaline earth cations, especially Ca, Sr or Ba.

The material (Ba,Sr,Ca)S:Eu can also be indicated as MS:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca).

Further, the material (Ba,Sr,Ca)$_2$Si$_5$N$_8$:Eu can also be indicated as M$_2$Si$_5$N$_8$:Eu, wherein M is one or more elements selected from the group consisting of barium (Ba), strontium (Sr) and calcium (Ca); especially, M comprises in this compound Sr and/or Ba. In a further specific embodiment, M consists of Sr and/or Ba (not taking into account the presence of Eu), especially 50 to 100%, more especially 50 to 90% Ba and 50 to 0%, especially 50 to 10% Sr, such as $Ba_{1.5}Sr_{0.5}Si_5N_8$:Eu (i.e. 75% Ba; 25% Sr). Here, Eu is introduced and replaces at least part of M, i.e. one or more of Ba, Sr, and Ca.

Likewise, the material (Ba,Sr,Ca)AlSiN$_3$:Eu can also be indicated as MAlSiN$_3$:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca).

Eu in the above indicated luminescent materials is substantially or only in the divalent state, as is known to the person skilled in the art.

The garnet type luminescent material may especially be applied as first luminescent material.

The term "luminescent material" herein especially relates to inorganic luminescent materials, which are also sometimes indicated as phosphors. These terms are known to the person skilled in the art.

The term "luminescent material" especially refers to a material that can convert first radiation, especially one or more of UV radiation and blue radiation, into second radiation. In general, the first radiation and second radiation have different spectral power distributions. Hence, instead of the term "luminescent material", also the terms "luminescent converter" or "converter" may be applied. In general, the second radiation has a spectral power distribution at larger wavelengths than the first radiation, which is the case in the so-called down-conversion. In specific embodiments, however the second radiation has a spectral power distribution with intensity at smaller wavelengths than the first radiation, which is the case in the so-called up-conversion. In embodiments, the "luminescent material" may especially refer to a material that can convert radiation into e.g. visible and/or infrared light. For instance, in embodiments the luminescent material may be able to convert one or more of UV radiation and blue radiation, into visible light. The luminescent material may in specific embodiments also convert radiation into infrared radiation (IR). Hence, upon excitation with radiation, the luminescent material emits radiation. In general, the luminescent material will be a down converter, i.e. radiation of a smaller wavelength is converted into radiation with a larger wavelength ($\lambda_{ex}<\lambda_{em}$), though in specific embodiments the luminescent material may comprise down-converter luminescent material, i.e. radiation of a larger wavelength is converted into radiation with a smaller wavelength ($\lambda_{ex}>\lambda_{em}$). In embodiments, the term "luminescence" may refer to phosphorescence. In embodiments, the term "luminescence" may also refer to fluorescence. Instead of the term "luminescence", also the term "emission" may be applied. Hence, the terms "first radiation" and "second radiation" may refer to excitation radiation and emission (radiation), respectively. Likewise, the term "luminescent material" may in embodiments refer to phosphorescence and/or fluorescence. The term "luminescent material" may also refer to a plurality of different luminescent materials.

Hence, the luminescent material may luminesce upon excitation with radiation, such as selected from one or more wavelengths selected from the range of 200-2000 nm, such as 300-1500 nm. Hence, the term "converter material" may especially also refer to a light converter element that at least partly absorbs one or more wavelengths in the UV, visible, or infrared, especially one or more wavelengths selected from the range of 200-2000 nm, such as 300-1500 nm, and converts such radiation, at least partly, into luminescence, especially at another wavelength.

Especially, a luminescent material is or comprises an active species. Here, the term "active species" may refer to an atom, ion, molecular group, or molecule that effectively is able to convert the light source light into luminescent material light, and thus provides the converter function to the luminescent material (or converter material).

When a solid state light source is applied for essentially only generating the cyan-like light, due to binning, there may be a variation in the color point obtained. It appears that this has a relatively high impact on the resultant color point and/or on the resultant correlated color temperature.

Herein (see also above), a solution is provided by using a luminescent material that emits in the cyan-like wavelength range. Alternatively or additionally, amongst others it is herein also suggested to use at least two different light sources to generate the second light.

Hence, in embodiments the light generating device comprises a first light source configured to generate first light source light comprising the first light, a second light source configured to provide second light source light, and a third light source configured to generate third light source light spectrally different from the second light source light, wherein second light source light has a second peak maximum ($\lambda$max2), wherein the third light source light has a third peak maximum ($\lambda$max3), especially differing at least 5 nm. Hence, especially in such embodiments the second light comprises the second light source light and the third light source light, more especially the second light essentially consists of the second light source light and the third light source light.

In embodiments, the second light source comprises a solid state light source, wherein the third light source comprises a solid state light source.

Especially, in such embodiments the second light source and the third light source may be from different bins. The bin may have a wavelength range of e.g. 5 nm, but especially at maximum 10 nm.

When referring to solid state light sources, the phrase "different spectral distributions" and similar phrases may especially refer to solid state light sources that are at least of different bins. More especially, in specific embodiments the second (solid state) light source light and the third (solid state) light source light may have peak wavelength differences of at least 10 nm, such as at least 20 nm, like at least 25 nm. In specific embodiments the second (solid state) light source light and the third (solid state) light source light may have peak wavelength differences selected from the range of 5-40 nm, such as selected from the range of 10-35 nm, like selected from the range of 10-30 nm.

In an alternative definition (see also below), in embodiments the second light source light has a second centroid wavelength, wherein the third light source light has a third centroid wavelength differing at least 5 nm from the second light source light.

For instance, in specific embodiments the second peak maximum ($\lambda$max2) is selected from the range of 470-500 nm, and wherein the third peak maximum ($\lambda$max3) is selected from the range of 500-520 nm (or even from the range of 500-530 nm).

Especially, both peak wavelengths are in the cyan-like wavelength range, even more especially at least one is in the cyan wavelength range. Likewise, especially both centroid wavelengths are in the cyan-like wavelength range, even more especially at least one is in the cyan wavelength range.

The second light source and the third light source may in embodiments have a fixed setting (i.e. on or off). Would the first light source also have a single setting (i.e. only on or off), then the light generating device would not be controllable, and there would be only one control mode. However, two or more of these light sources may be controllable, thereby providing a controllable light generating device. Would the second light source and third light source be controllable, the color point of the second light may be controllable, and also the contribution of the second light may be controllable. Hence, in specific embodiments the second light source and the third light source are controllable. Alternatively, or especially additionally, the first light source may also be controllable.

As can be derived from the above, the term "first light source" may also refer to a plurality of (different) light sources, which together may provide the first light source light. Likewise, the term "second light source" may also refer to a plurality of (different) light sources, which together may provide the second light source light. Likewise, the term "third light source" may also refer to a plurality of (different) light sources, which together may provide the third light source light.

In the above embodiment(s), the second light source light and the third light source light may especially be solid state light sources, like LEDs, without luminescent material(s) for converting part of the second light source light and/or third light source light.

In further specific embodiments, the above indicated second light source and/or third light source, that together may provide the second light may each independently comprise a solid state light source with a luminescent material that converts at least part of the solid ate light source light into luminescent material light.

Hence, in embodiments the second light source is configured to provide second light source light, wherein the second light source comprises a second solid state light source configured to provide second solid state light source light and a second luminescent material configured to convert at least part of the second solid state light source light into second luminescent material light, wherein the second light source light comprises second luminescent material light and optionally (remaining) second solid state light source light.

Alternatively or additionally, in embodiments the third light source is configured to provide third light source light, wherein the third light source comprises a third solid state light source configured to provide third solid state light source light and a third luminescent material configured to convert at least part of the third solid state light source light into third luminescent material light, wherein the third light source light comprises third luminescent material light and optionally (remaining) third solid state light source light.

As can be derived from the above, the spectral distribution of the second light source light and the third light source light (in the first control mode) differ from each other, such as having different spectral centroid wavelengths. The centroid wavelength is the wavelength that divides the integral of a spectrum into two equal parts. For a symmetrical spectrum, the peak maximum and the centroid wavelength are identical. Note that even though spectra are in general indicated on a linear wavelength scale in nm, for the purpose of defining maxima, centroid wavelengths, etc., a scale scaling with a linear energy scale may be used.

Hence, in embodiments the light generating device comprises a first light source configured to generate first light source light comprising the first light, a second light source configured to provide second light source light comprising second luminescent material light, and a third light source configured to generate third light source light comprising third luminescent material light, wherein the third light source light is spectrally different from the second light source light, wherein in embodiments the second light source light has a second centroid wavelength, wherein the third light source light has a third centroid wavelength differing at least 5 nm from the second light source light. Hence, especially in such embodiments the second light comprises the second light source light and the third light source light, more especially the second light essentially consists of the second light source light and the third light source light. As will be clear from the above, at least one of the centroid wavelengths, especially at least both, are within the wavelength range of 470-520 nm.

Therefore, in embodiments the light generating device may comprise a first light source configured to generate first light source light comprising the first light, a second light source configured to provide second light source light, wherein the second light source light comprises second luminescent material light, and a third light source configured to generate third light source light, wherein the third light source light comprises third luminescent material light, and wherein the third light source light is spectrally different from the second light source light, wherein the second light source light has a second centroid wavelength and wherein the third light source light has a third centroid wavelength differing at least 5 nm from the second centroid wavelength of the second light source light.

In the above embodiment(s), the second light source light and the third light source light may especially be solid state light sources, like PC-LEDs, with luminescent material(s) for converting part of the second light source light and/or third light source light. The term "PC" herein refers to "phosphor-converted".

Especially, the device may comprise one or more solid state light source that provide the device light. One or more solid state light source may comprise a luminescent material. Luminescent material may also be configured external of the solid state light sources. Hence, in embodiments the device comprises one or more solid state light sources and one or more luminescent materials, configured to convert at least part of the light source light generated by the one or more solid state light sources (in the first control mode), wherein the comprises one or more solid state light sources and one or more luminescent materials are configured to provide the device light in the first control mode.

As indicated above, in specific embodiments the spectral distribution of the device light may be controllable. This may e.g. be controlled via a (graphical) user interface. Alternatively or additionally, the spectral distribution may depend upon the time, such as daytime and/or period of the year. Yet further, alternatively or additionally the spectral distribution may depend on a sensor signal of a sensor, such as a daylight sensor, a light sensor, a MEF value or MEF related value sensor, a movement (or presence) sensor, etc. To this end, the light generating device may comprise or be functionally coupled to a control system.

Hence, in embodiments the invention provides a lighting generating device that can provide (white) device light having adjustable melatonin suppression effects. To this end, the light generating device has controllable device light. In embodiments, during use the MEF value (or related value) may be controlled. With the term "related value" e.g. MDEF value or MELR value is meant.

Therefore, in yet a further aspect the invention provides a lighting system comprising the light generating device as defined herein, wherein the spectral distribution of the device light is controllable, wherein the lighting system further comprises a control system and an input device selected from the group consisting of a user interface, a time device, and a sensor, and wherein the control system is configured to control the spectral distribution of the device light in response to a signal of the input device.

In such embodiments, wherein the device light is controllable, the device light may be controlled in related to the optical properties, such as spectral distribution, color point, color temperature, etc. For instance, based on a signal of the input device, the control system controls the spectral distribution of the device light. The control system may comprise or have access to a database with predefined relations between spectral distribution and one or more of a time signal and a sensor signal.

The term "input device" may also refer to a plurality of different input devices. The time device may comprise one or more of a timer and a clock. As indicated above, the sensor may be a daylight sensor, a light sensor, a MEF value or MEF related value sensor, a movement (or presence) sensor, etc. etc. In embodiments, the MEF value or MEF related value sensor may refer to an MDEF sensor or an MDEF related sensor, such as a MELR sensor.

When the distribution of the device light is controllable, the control system may provide at least the first control mode (in addition to one or more other modes), wherein the device light as specified herein is provided.

The term "controlling" and similar terms especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element. The controlling of the element can be done with a control system, which may also be indicated as "controller". The control system and the element may thus at least temporarily, or permanently, functionally be coupled. The element may comprise the control system. In embodiments, the control system and element may not be physically coupled. Control can be done via wired and/or wireless control. The term "control system" may also refer to a plurality of different control systems, which especially are functionally coupled, and of which e.g. one control system may be a master control system and one or more others may be slave control systems. A control system may comprise or may be functionally coupled to a user interface.

The term "light source" may refer to a semiconductor light-emitting device, such as a light emitting diode (LEDs), a resonant cavity light emitting diode (RCLED), a vertical cavity laser diode (VCSELs), an edge emitting laser, etc.

The term "light source" may also refer to an organic light-emitting diode, such as a passive-matrix (PMOLED) or an active-matrix (AMOLED). In a specific embodiment, the light source comprises a solid state light source (such as a LED or laser diode). In an embodiment, the light source comprises a LED (light emitting diode). The term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of semiconductor light sources may be configured on the same substrate. In embodiments, a COB is a multi LED chip configured together as a single lighting module. The term "light source" may also relate to a plurality of light sources, such as 2-2000 solid state light sources.

The term "light generating device" as used herein may in embodiments refer to such light source or to a plurality of such light sources. For instance, the light generating device may comprise a COB or may comprise two or more different COBs.

The invention also provides (in an aspect) a method of (indoor) lighting wherein with two or more sources of light, (device) light is generated that is white and that has a cyan-like spectral component. The invention also provides (in an aspect) a method of (indoor) lighting wherein with two or more sources of light, (device) light is generated that is white, wherein the (device) light has a MDEF value of ≥5.43-9.31*v', wherein the MDEF is defined as:

$$MDEF = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3a)}$$

wherein SPD(λ) is the spectral power distribution of the light emitted by a light generating device, m(λ) is the melanopic sensitivity function, the V(λ) is the photopic sensitivity.

The invention also provides (in an aspect) a method of (indoor) lighting wherein with a light generating device comprising one or more solid state light sources and optionally one or more luminescent materials, (device) light is generated that is white and that has a cyan-like spectral component. The invention also provides (in an aspect) a method of (indoor) lighting wherein with a light generating device comprising one or more solid state light sources and optionally one or more luminescent materials, (device) light is generated that is white, wherein the (device) light has a MDEF value of ≥5.43-9.31*v', wherein the MDEF is defined as:

$$MDEF = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3a)}$$

wherein SPD(λ) is the spectral power distribution of the light emitted by a light generating device, m(λ) is the melanopic sensitivity function, the V(λ) is the photopic sensitivity.

Alternatively, instead (or in addition) of the MDEF condition the MELR condition may be applied (see elsewhere herein).

As indicated above, increasing the iPRGCs stimulation can be done by increasing the intensity, or by increasing the CCT (blue enriched) as that gives higher MDEF. Both options may have limitations due to unwanted side effects like e.g. increasing glare and/or people may dislike relatively high CCTs. Alternatively, a high MDEF for neutral white light can be achieved by enhancing the cyan intensity in the spectrum, as the iPRGC sensitivity peaks in the cyan region rather than the blue. This could in embodiments be done by adding a phosphor that emits cyan light. Another option to achieve a cyan-enhanced neutral-white light source may be by combining warm-white and cyan LEDs. Because of the spread in output of LEDs, it may be desirable that the current ratio through the cyan and the white LEDs may especially be controlled to meet light source color point spread. For this, the cyan and white LEDs can e.g. be placed in separate strings which may individually be controlled. This may require a multi-channel driver and a system with controls.

Surprisingly, it was also found that solutions for a neutral-white (e.g. ~4000K) with high MDEF (~0.85) light source can be provided, wherein e.g. cyan and warm-white LEDs can be in a single channel, while still meeting light-technical requirements such as one or more of CRI, R9 and color point spread. A very high MDEF while still maintaining good color quality (CRI 80 and good white appearance) was obtained by choosing the proper dominant wavelength cyan LED, combining it with the proper set of warm-white LEDs, at the proper color point and with the proper flux relative to the cyan LED flux. This may also yield a single-channel solution, which is therefore easy to use.

In an aspect, the invention also provides a light generating device comprising a LED string, wherein the LED string comprises N LEDs, wherein the N LEDs in the LED string are provided as at least n groups of subsets of k LEDs, wherein the k LEDs are configured in series, wherein two or more of the n groups of subsets of k LEDs are configured in parallel in the LED string, wherein the k LEDs in the n groups are selected from white LEDs and cyan LEDs, wherein n*k≤N, wherein n≥2, wherein k≥2, wherein N≥4, wherein the N LEDs at least comprise one or more white LEDs and one or more cyan LEDs, wherein the LED string in embodiments is configured in a first control mode the device light as defined herein. The phrase "at least n groups of subsets of k LEDs", and similar phrases, may also refer to z sets of each at least n groups of subsets of k LEDs. Sets may (or may not) differ in number of n groups and/or number of subsets of k LEDs in the groups.

Especially, the phrase "at least n groups of subsets of k LEDs", and similar phrases, refer to n groups of identical subsets. Each subset may comprise one or more white LEDs or one or more cyan LEDs, or one or more white LEDs and one or more cyan LEDs. Hence, the k LEDs may be identical LEDs, like all white (for the first light), or all cyan (for the second light), or may comprise different LEDs (configured in series); however, the groups which are configured in parallel include identical groups.

Other LEDs than the cyan and white LEDs may be available in the string, hence n*k≤N.

As indicated above, in specific embodiments the second light may have a dominant wavelength selected from the range of 470-510 nm, such as selected from the range of 474-500 nm, even more especially selected from the range of 474-490 nm, like 475-490 nm, such as 475-488 nm.

Alternatively or additionally, especially the first light may have a correlated color temperature selected from the range of 2300-4600 K, especially 2500-4500 K, like e.g. selected from the range of 2700-4100 K.

Hence, in an aspect the invention provides a light generating device configured to generate in a first control mode device light, wherein the light generating device comprises (i) a first source of first light, especially having a correlated color temperature selected from the range of 2500-4500 K, and (ii) a second source of second light, different from the first light, wherein the second light comprises cyan-like light having a dominant wavelength selected from the range of 470-510 nm, such as selected from the range of 474-500 nm, even more especially selected from the range of 474-490 nm, like 475-488 nm; wherein the device light comprises the first light and the second light, and wherein in the first control mode the device light is white light, and wherein the light generating device is configured to provide in the first control mode the device light, especially in embodiments having a MDEF value of $\geq 5.43-9.31*v'$, wherein SPD($\lambda$) is the spectral power distribution of the light emitted by a light generating device (100), m($\lambda$) is the melanopic sensitivity function, the V($\lambda$) is the photopic sensitivity.

On the CIE (1931) color coordinate space, a straight line drawn between the point for a given color and the point for the color of the illuminant can be extrapolated out so that it intersects the perimeter of the space in two points. The point of intersection nearer to the color in question reveals the dominant wavelength of the color as the wavelength of the pure spectral color at that intersection point. The point of intersection on the opposite side of the color space gives the complementary wavelength, which when added to the color in question in the right proportion will yield the color of the illuminant (since the illuminant point necessarily sits between these points on a straight line in CIE space, according to the definition just given). In situations where no particular illuminant is specified, it is common to discuss dominant wavelength relative to one of several "white" standard illuminants, such as equal-energy (flat spectrum) or a color temperature such as 6500K.

In specific embodiments, the second light may have a spectral power Wopt/1100 lumen, wherein the first light has a correlated color temperature $CCT_{211}$, wherein a value of the Wopt/1100 lumen is selected from the range of:

$$0.03+0.00019*CCT_{211}*\leq Wopt/1100 \text{ lumen}\leq 0.12+0.000208*CCT_{211}$$

wherein Wopt/1100 lumen refers to the value of the radiometric contribution of second light per 1100 Lm of device light (i.e. sum S of first and second light), and wherein $CCT_{211}$ refers to the value of the color temperature in Kelvin. For instance, when the CCT of the first light is 3000 K, then the value is 3000, and the value of Wopt/1100 lumen is in the range of 0.6-1.044. Hence, per 1100 lumen of the first light, 0.6-1.044 Watt of the second light, especially having a dominant wavelength in the range of 474-500 nm, such as in the range of 474-488 nm, such as 475-488 nm, may be provided. Together, the first light and the second light may in the first control mode provide the device light. Hence, in embodiments the second light has a spectral power Wopt/1100 lumen, wherein the first light has a correlated color temperature $CCT_{211}$, wherein Wopt/1100 lumen refers to the value of the radiometric contribution in Watt of the second light per 1100 Lumen of device light, wherein $CCT_{211}$ refers to the value of the correlated color temperature in Kelvin of the first light, and wherein a value of Wopt/1100 lumen is selected from the range of: $0.03+0.00019*CCT_{211}*\leq Wopt/1100 \text{ lumen}\leq 0.12+0.000208*CCT_{211}$.

Further, it appears that within the CCT range of about 2500-4200 K, especially about 2700-4000 K, the dominant wavelength range DWL in nanometer of the second light may be defined by the formula: $474<DWL<(510-0.008*CCT)$. Here, DWL refers to the value of the dominant wavelength (in nm), 474 refers to the lower limit of 474 nm, and CCT refers to the value of the correlated color temperature of the first light. For instance, when the CCT is 3500 K, the formula is: $474<DWL<(510-0.008*3500)$, i.e. the dominant wavelength range DWL is between 474 nm and 482 nm.

In yet a further aspect, the invention also provides a computer program product, when running on a computer which is functionally coupled to or comprised by lighting system configured to control (in a control mode (of the computer)) the spectral distribution of the device light (as defined herein), is capable of bringing about the method(s) as defined herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

The schematic drawings are not necessarily to scale. Schematic drawings may show combinations of features of different embodiments, for the sake of efficiency.

DETAILED DESCRIPTION OF THE EMBODIMENTS

Figure 1A:
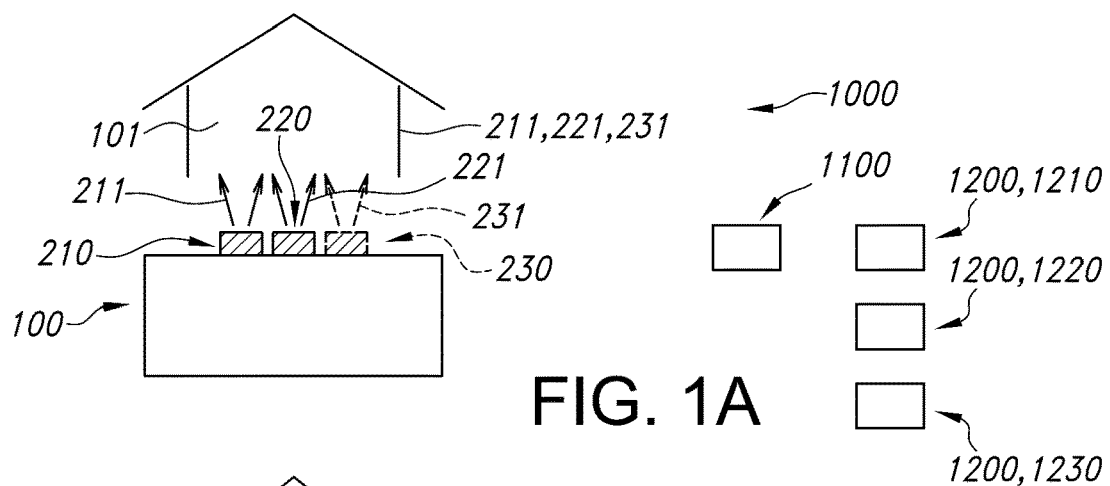
FIGS. 1A-1B schematically depict some embodiments and aspects of a light generating device (or lighting system)

FIG. 1A schematically depicts an embodiment of a light generating device 100 comprising (i) a first source 210 of first light 211, and (ii) a second source 220 of second light 221, different from the first light 210.

In the embodiment schematically depicted, the light generating device 100 comprises a first source 210 of first light 211, a second source 220 of second light 221, and optionally a third source 230 of third light 231. Dependent upon the desired mode of execution, the third source may contribute to the device light 101. Here, the embodiments is shown wherein the third light 231 contributes to the device light 101.

In embodiments, the first source 210 may be configured to generate first white light 211. The second source 220 may be configured to provide cyan-like light second light. The third source 230 may be configured to generate a third light that is essentially red, e.g. for a better color rendition and/or warm white. In embodiments, the second source and third source may together provide the second light.

Figure 1B:
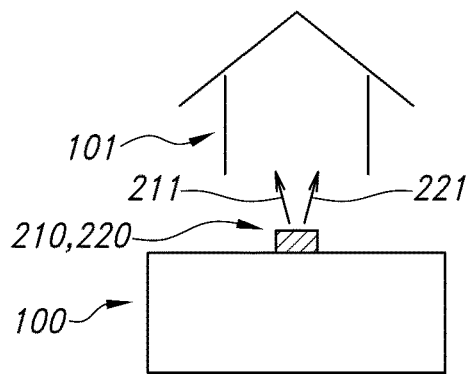

FIG. 1B schematically depicts an embodiment wherein a single light source may have the functionality of the first source of light 210 and the second source of light 220.

Some more detailed examples are described in relation to FIGS. 2A-2F.

In relation to the embodiment of FIG. 1A, but this may relate to essentially all schematically depicted embodiments of FIGS. 1A-2F, also a lighting system 1000 comprising the light generating device 100 is schematically depicted. The lighting system 1000 may thus comprise the light generating device 100 as defined herein. The spectral distribution of the device light 101 is controllable. The lighting system 1000 further comprises a control system 1100 and an input device 1200 selected from the group consisting of a user interface 1210, a time device 1220, and a sensor 1230. Especially, the control system is 1100 is configured to control the spectral distribution of the device light 101 in response to a signal of the input device.

Herein, schematically—for the sake of clarity—the elements of the control system 1100, the user interface 1210, the time device 1220, and the sensor 1230 are depicted as items physically separated from the light generating device. However, in embodiments one or more of these elements may be integrated in the light generating device.

Further, the lighting system 1000 may comprise a plurality of light generating devices 100 (not depicted), that are controlled the control system 1100.

Figure 2A:
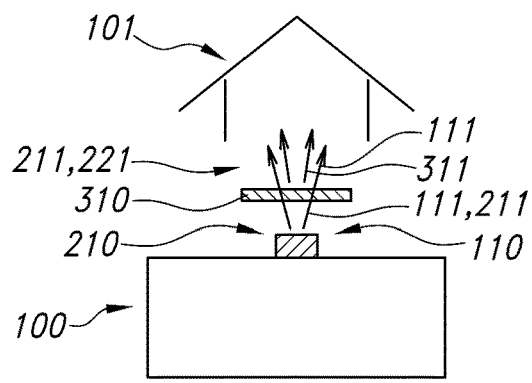
FIGS. 2A-2I schematically depict some further embodiments and aspects of a light generating device (or lighting system)

FIG. 2A schematically depicts an embodiment of a light generating device 100 comprising (i) a first source 210 of first light 211, and (ii) a second source 220 of second light 221, different from the first light 210.

In the embodiment schematically depicted, the light generating device 100 comprises a first light source 110 configured to generate first light source light 111, such as white light.

In the embodiment schematically depicted, the light generating device comprises a first luminescent material 310 configured to convert part of the first light source light 111 into the first luminescent material light 311, for instance light essentially consisting of cyan-like light. Hence, the second light 221 comprises at least part of the first luminescent material light 311. For instance, the second light 221 may essentially consist of the first luminescent material light. The second light 221 comprises cyan-like light having a wavelength selected from the range of 470-520 nm.

Hence, FIG. 2A schematically depicts an embodiment of the light generating device 100 comprises a first light source 110 configured to generate first light source light 111 comprising the first light 211, and a first luminescent material 310 configured to convert part of the first light source light 111 into the first luminescent material light 311, wherein the second light 221 comprises at least part of the first luminescent material light 311.

Figure 2B:
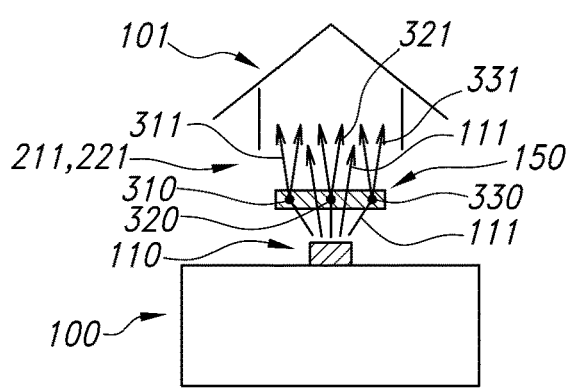

FIG. 2B schematically depicts an embodiment of a light generating device 100 comprising (i) a first source of first light 211, and (ii) a second source of second light 221, different from the first light 211.

In the embodiment schematically depicted, the light generating device 100 comprises a first light source 110 configured to generate first light source light 111, such as blue light.

In the embodiment schematically depicted, the light generating device comprises a first luminescent material 310 configured to convert part of the first light source light 111 into the first luminescent material light 311, for instance light essentially consisting of cyan-like light. Hence, the second light 221 comprises at least part of the first luminescent material light 311. For instance, the second light 221 may essentially consist of the first luminescent material light. The second light 221 comprises cyan-like light having a wavelength selected from the range of 470-520 nm.

Further, in the embodiment schematically depicted, the light generating device 100 comprises a second luminescent material 320 configured to convert part of the first light source light 111 into second luminescent material light 321, e.g. yellow light and optionally one or more further luminescent materials 330 configured to convert part of first light source light 111 into further luminescent material light 331. Hence, the first light 211 may be essentially white light, and may essentially consist of at least part of the light source light 111, second luminescent material light 321 and optionally further luminescent material light 331.

In this way, in a first operation mode, the device light 101 comprises the first light source light 111, the first luminescent material light 311, the second luminescent material light 321, and the optional further luminescent material light 331.

In the embodiment schematically depicted, the light generating device 100 comprises a luminescent element 150 comprising the first luminescent material 310, the second luminescent material 320, and the optional one or more further luminescent materials 330. The luminescent body may e.g. be a multi-layer element, a ceramic body, a resin based body, etc. Hence, in embodiments the device light 101 comprises the first light 211 and the second light 221. Especially, in the first control mode the first light 211 is white light and also the device light 101 is white light. These both types of light have different spectral distribution, as the device light is enriched with cyan-like light compared to the first light.

In general, would the light generating device 100 of FIG. 2B be controllable, then basically the spectral properties of the device light 101 will not vary much.

Figure 2C:
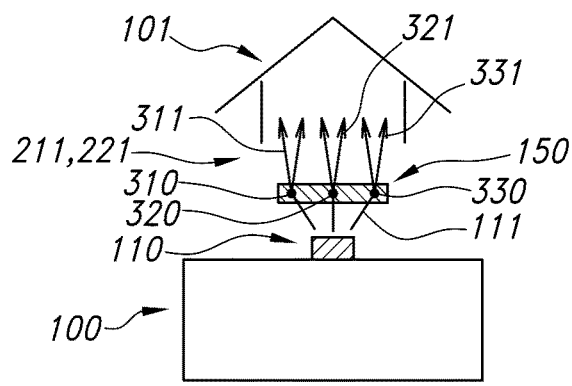

FIG. 2C schematically depicts essentially the same embodiment as FIG. 2B. However, here the device light 101 does (essentially) not comprise the first light source light 111. For instance, the first light source may be a UV LED.

FIG. 2C also schematically depicts an embodiment of a light generating device 100 comprising (i) a first source of first light 211, and (ii) a second source of second light 221, different from the first light 210. In the embodiment schematically depicted, the light generating device 100 comprises a first light source 110 configured to generate first light source light 111, such as UV light.

In the embodiment schematically depicted, the light generating device comprises a first luminescent material 310 configured to convert part of the first light source light 111 into the first luminescent material light 311, for instance light essentially consisting of cyan-like light. Hence, the second light 221 comprises at least part of the first luminescent material light 311. For instance, the second light 221 may essentially consist of the first luminescent material light. The second light 221 comprises cyan-like light having a wavelength selected from the range of 470-520 nm.

Further, in the embodiment schematically depicted, the light generating device 100 comprises a second luminescent material 320 configured to convert part of the first light source light 111 into second luminescent material light 321, e.g. blue light and optionally one or more further luminescent materials 330 configured to convert part of first light source light 111 into further luminescent material light 331, e.g. yellow, or yellow+red, or green+red. Hence, the first light 211 may be essentially white light, and may essentially consist of the second luminescent material light 321 and the further luminescent material light 331.

In this way, in a first operation mode, the device light 101 comprises the first the first luminescent material light 311, the second luminescent material light 321, and the further luminescent material light 331.

In the embodiment schematically depicted, the light generating device 100 comprises a luminescent element 150 comprising the first luminescent material 310, the second luminescent material 320, and the one or more further luminescent materials 330. The luminescent body may e.g. be a multi-layer element, a ceramic body, a resin based body, etc. Hence, in embodiments the device light 101 comprises the first light 211 and the second light 221. Especially, in the first control mode the first light 211 is white light and also the device light 101 is white light. These both types of light have different spectral distribution, as the device light is enriched with cyan-like light compared to the first light.

Figure 2D:
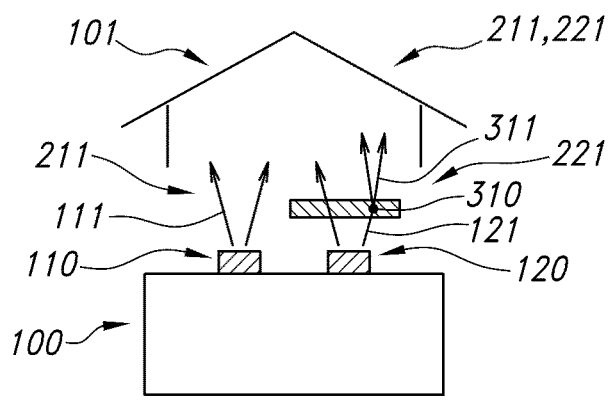

FIG. 2D schematically depicts an embodiment wherein the light generating device 100 comprises (i) a first light source 110 configured to generate first light source light 111 comprising the first light 211, (ii) a second light source 120 configured to generate second light source light 121, and (iii) a first luminescent material 310 configured to convert at least part of the second light source light 121 into first luminescent material light 311. The second light 221 comprises at least part of the first luminescent material light 311 and optionally (unconverted) second light source light 121.

Such embodiment may allow controllability of the spectral composition of the device light 101.

Figure 2E:
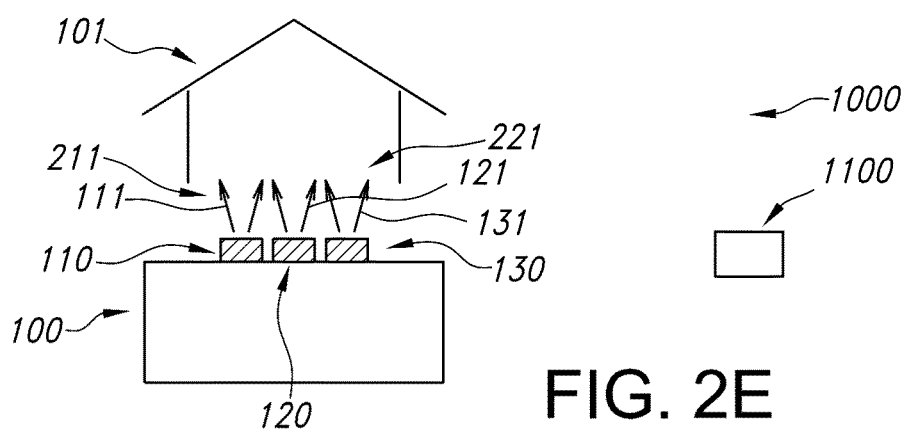
Figure 2F:
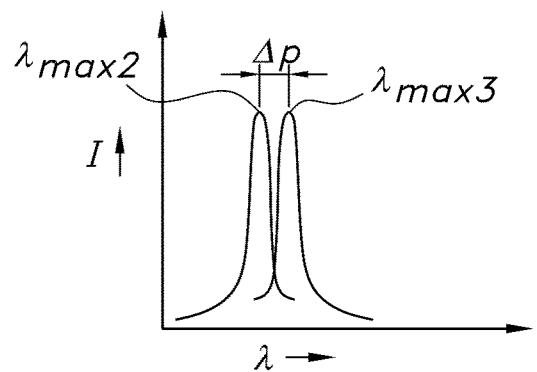

FIG. 2E schematically depicts an embodiment wherein e.g. the light generating device 100 comprises a first light source 110 configured to generate first light source light 111 comprising the first light 211, a second light source 120 configured to provide second light source light 121, and a third light source 130 configured to generate third light source light 131 spectrally different from the second light source light 121. Especially, the second light source light 121 may have a second peak maximum λmax2, wherein the third light source light 131 has a third peak maximum λmax3 differing at least 5 nm, see also FIG. 2F. For instance, the second peak maximum λmax2 is selected from the range of 475-480 nm, and wherein the third peak maximum λmax3 is selected from the range of 500-520 nm. The second light 221 comprises the second light source light 121 and the third light source light 131.

For instance, the second light source 120 may comprise a solid state light source, the third light source 130 may comprise a solid state light source, and the second light source 120 and the third light source 130 may be from different bins.

In embodiments, the second light source 120 and the third light source 130 may be controllable, but this is not necessarily the case.

Instead of solid state light sources wherein the light emanates from the die and there is substantially no conversion, it may also be possible to include in one or more of the light sources a luminescent material. For instance, both the second light source and the third light source may comprises phosphor converted LEDs. Hence, FIG. 2E may also show an embodiment, wherein the light generating device 100 comprises a first light source 110 configured to generate first light source light 111 comprising the first light 211, a second light source 120 configured to provide second light source light 121, wherein the second light source light 121 comprises second luminescent material light, and a third light source 130 configured to generate third light source light 131, wherein the third light source light 131 comprises third luminescent material light, and wherein the third light source light 131 is spectrally different from the second light source light 121. Especially, the second light source light 121 has a second centroid wavelength and wherein the third light source light 131 has a third centroid wavelength differing at least 5 nm from the second centroid wavelength of the second light source light 121 analogues to FIG. 2F.

Amongst others, an aspect of the invention is to increase the MDEF of a light source by an increase of intensity in the cyan region, thus enabling a higher melanopic stimulus. Phosphor converted cyan LEDs (pc-Cyan) are used to enrich a white spectrum in the cyan region. In the present invention pc-Cyan LEDs are mixed with/added to standard warm white LEDs. Some blue leakage of the pc-Cyan LED may be required (otherwise tuning along the BBL is not possible); these partial-conversion LEDs may be more efficient than full-conversion pc-Cyan LEDs.

The color point of the cyan LEDs appears to be strongly dependent on the wavelength of the LED. A 1 nm shift of the peak wavelength of a cyan LED, induces a color point shift (of the cyan LED) of ~12 pts in v' (~12 SDCM). When combining this with a white LED of 3000K and targeting 4000K for the combination, this induces a color point spread of ~1.5 SDCM/nm variation of the peak wavelength of cyan. Using a lower CCT (warmer) white LED, or targeting a higher CCT will increase the color spread. Typical direct LED bin distributions are at least 5 nm wide, introducing a color point spread due to peak wavelength variation of >7 SDCM (in addition to the color point spread introduced by the white LED). In addition to peak wavelength distribution of the cyan LEDs, the peak wavelength of cyan LED will also shift with temperature (inevitable effect, band gap related), introducing an additional color point spread.

Figure 2G:
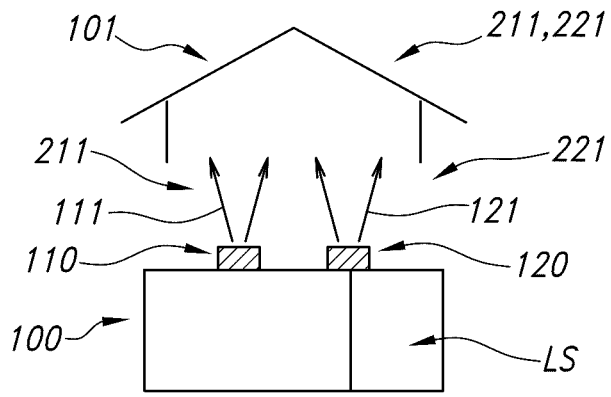

FIG. 2G schematically depicts a lighting generating device 100 comprising a first light source 110 and a second light source 120. The first light source 110 is configured to generate first light source light 111; the second light source 120 is configured to generate second light source light 121. Together, they may provide the lighting device light 101. For instance, the first light source light 111 may comprise the first light 211 and the second light source light 121 may comprise the second light 221. In a further variant, the first light source 110 and the second light source 120 may be in a string LS. There may be a plurality of different (or identical) strings.

Figure 2H:
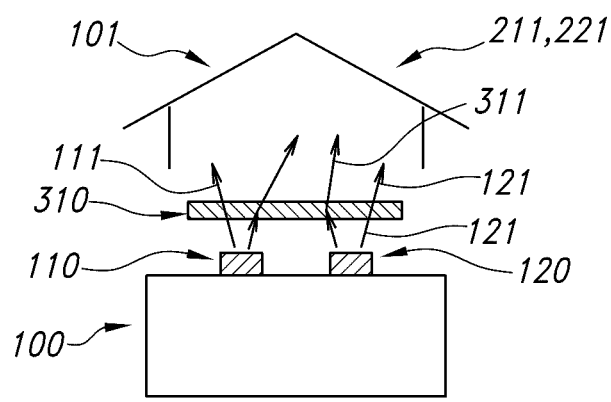
Figure 2I:
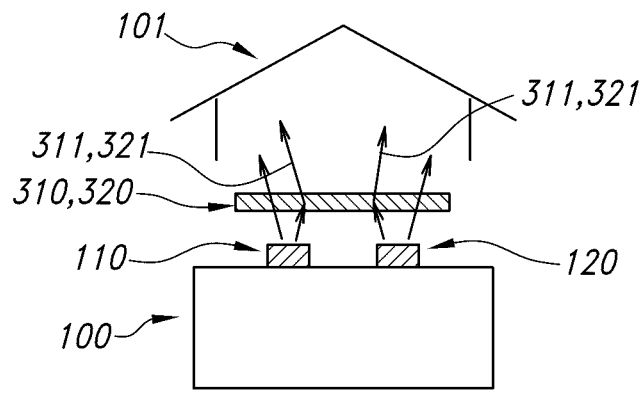

Referring to FIGS. 2H-2I, schematically lighting generating devices 100 are depicted comprising a first light source 110 and a second light source 120. The first light source 110 is configured to generate first light source light 111; the second light source 120 is configured to generate second light source light 121. Especially, the first light source 110 may be configured to generate blue first light source light 111, and the second light source 120 may be configured to generate cyan-like second light source light 121 having one or more wavelengths selected from the range of 470-520 nm. The light generating device 100 further comprises a first luminescent material 310, configured to convert part of one or more of the first light source light 111 and the second light source light 121 into first luminescent material light 311, and optionally a second luminescent material 320 see FIG. 2I, configured to convert part of one or more of the first light source light 111 and the second light source light 121 into second luminescent material light 321, wherein the first light source 110 and the second light source 120 are configured upstream of the first luminescent material 310 and the optional second luminescent material 320. Especially, in the first control mode the device light 101 is white light comprising the first light source light 111, the second light source light 121, the first luminescent material light 311 and the optional second luminescent material light 321. In embodiments, the first light source 110 and the second light source 120 may individually be controlled (with a control system).

Using a phosphor converted cyan LED could circumvent these problems. The color point spread of these pc-Cyan LEDs is expected to be as narrow as for the white LEDs. Color point shift with temperature is expected to be small (blue LED will shift with temperature, but effect is diminished by phosphor). A ±2 nm shift of the blue LED (used to pump the cyan phosphor) results in 1 SDCM color point shift in white spectrum (probably depends on the wavelength bin selected to excite the phosphor).

Figure 3:
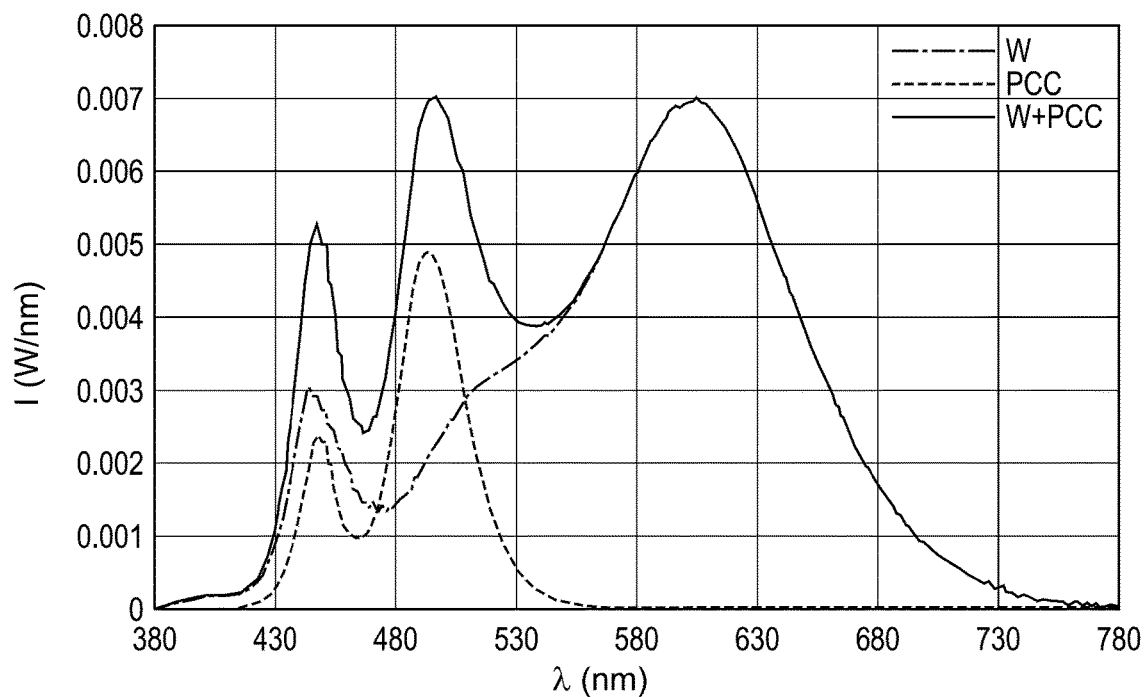
FIG. 3 shows a spectrum ("W") of a warm white LED with CRI 80, a spectrum (PCC (phosphor converted cyan LED)) of a solid state light source generating cyan-like light, based on a LED with luminescent material, and the resulting spectrum (W) containing the contribution of the warm white LED and the LED with luminescent material.

To induce a significant effect on the MDEF, the amount of cyan light added to the white spectrum may be high (see FIG. 3). After an initial increase in CRI, adding a narrow peak in this region leads to a decrease of the CRI. The phosphor emission will be broader than the emission of a direct emitter. As a result, when adding more cyan intensity the CRI does not decrease as fast as for direct cyan LED, so a higher MDEF is possible.

The cyan phosphor could also be added to the white LED phosphor mixture, leading to one LED with high melanopic efficiency. However, in particular the red phosphor absorbs (part of) the cyan emission. As a result, a higher phosphor load may be needed, resulting in a lower efficiency (increased scattering). For broader cyan phosphors also the shape of the emission could be altered, leading to lower melanopic efficiencies. Moreover, no color tuning would be possible when adding the cyan phosphor in the white LED.

FIG. 3 shows a spectrum ("W") of a warm white LED with CRI 80, a spectrum (PCC (phosphor converted cyan LED)) of a solid state light source generating cyan-like light, based on a LED with luminescent material, and the resulting spectrum (W) containing the contribution of the warm white LED and the LED with luminescent material.

Figure 4:
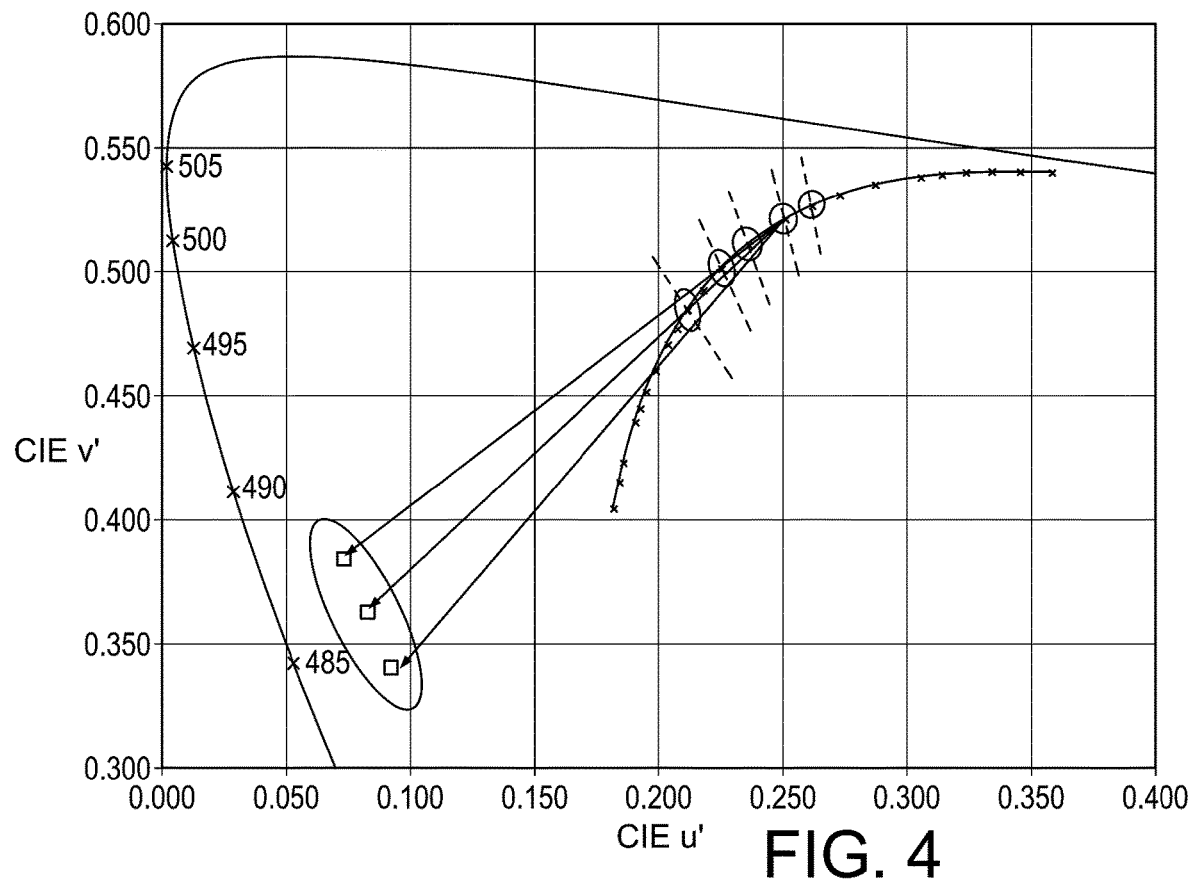
FIG. 4 shows an example of u' v' color diagram. Values close to the left axis indicate wavelength of monochromatic emission (CIELUV diagram)

The invention uses in embodiments the combination of warm white LEDs with a phosphor converted cyan LED. The cyan LED is partially converting blue to cyan. Color point of the pc-Cyan LED should be within the area defined in CIE v' of FIG. 4. This Figure especially applies to the application of the cyan phosphor $ML_2O_2N_2:Eu^{2+}$, wherein M is selected from the group consisting of Ca, Sr and Ba, and wherein L is selected from the group consisting of Si and Ge, wherein M at least comprises B, and wherein L at least comprises Si. More in general, the conditions can be found in FIG. 5.

Figure 5:
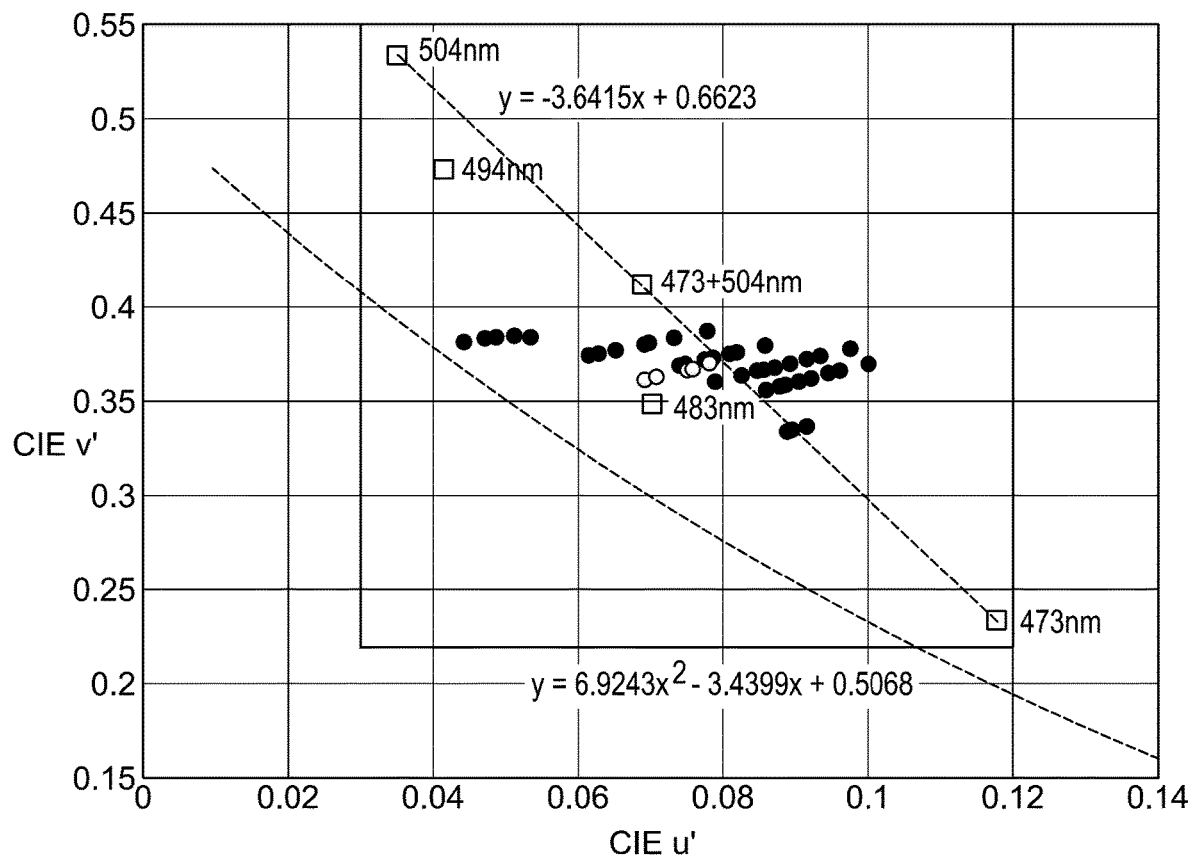
FIG. 5 depicts an embodiment of the desired range in the CIELUV color space of the second light, especially when applying phosphor converted LEDs to generate the cyan-like second light.

FIG. 5 schematically depicts the desired range in the CIELUV (1976) color space of the second light, especially when applying phosphor converted LEDs to generate the cyan-like second light. In such embodiments, the second light 221 has a color point (u';v') defined by the CIE u'v' area (0.03;0.22), (0.12;0.22), (0.03;0.55), and (0.12;0.55) in the CIE u'v' color space. The lowest dashed curve indicates part of the edge of the CIELUV color space. The values of the dashed curve in the graph complies with $y=6.9243*x^2-3.4399*x+0.5068$, wherein $x=u'$ and $y=v'$.

Other embodiments or variants may also be possible.

For instance, in an embodiment a warm white LED is combined with additional pc-Cyan LEDs is provided. In embodiments this may be a fixed system (i.e. essentially no controllability of the spectral properties of the resulting device light). The CIE v' of pc-Cyan LED(s) should especially be within the area defined in CIE v' of FIG. 5, such as in FIG. 4, see also above. Warm white light may be defined as white having a correlated color temperature of at maximum 3500 K.

For instance, in an embodiment a warm white LED is combined with one or more additional pc-Cyan LEDs is provided. Current through white and single cyan channel may be individually addressable. For instance, this may provide at least two set points on (or below) BBL. This may provide a set point with a low MDEF (=warm White) and with a high MDEF (e.g. 4500 K). CCTs in between these CCTs may be possible, but the color point may be off-BBL. As indicated above, CIE v' of pc-Cyan LED(s) should especially be within the area defined in CIE v' of FIG. 5, such as in FIG. 4, see also above.

For instance, in an embodiment a warm white LED with additional pc-Cyan LED(s) is provided. Current through white and the two or more cyan channels may especially be individually addressable. Tunable system with color point on (or below) BBL from warm white up to 5000 K. Higher dynamic range of MDEF compared to the tunable system of former embodiment (wider range of CCTs). The first PC-Cyan may especially be in the top of the area defined in CIE v' of FIG. 5, such as in FIG. 4; the second PC-Cyan may especially be in the bottom of FIG. 5, such as in FIG. 4.

Figure 6:
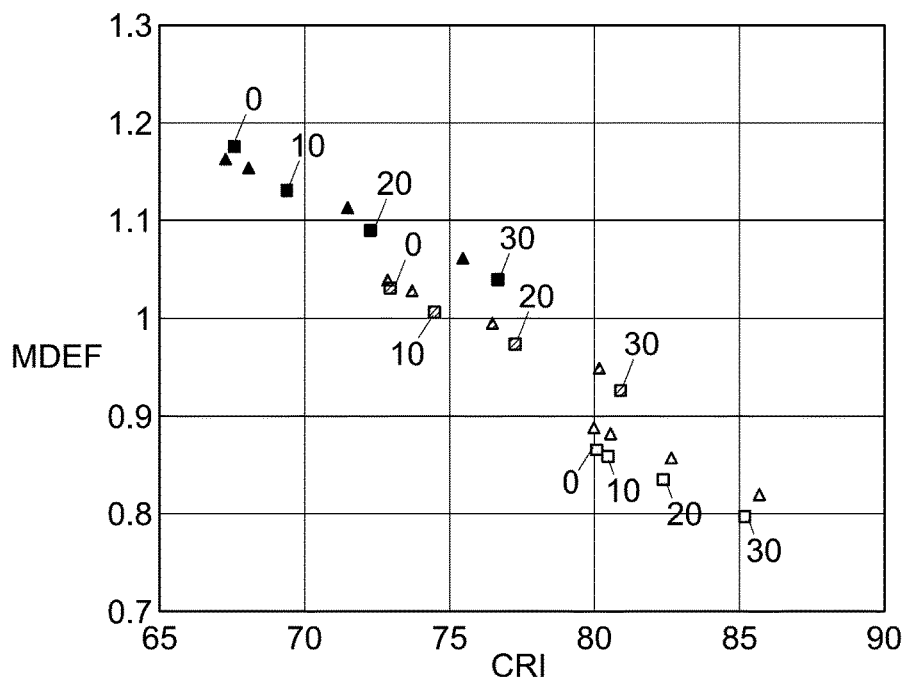
FIG. 6 depicts MDEF as a function of CRI for the combination of a 3000 K LED (CRI 80 LED cubes; CRI 90 LED triangles) and cyan LEDs. The labels indicate the peak wavelength difference, in nanometers, between the cyan LEDs used (0=single peak)

In alternative embodiments, using a combination of (at least) two cyan LEDs with different peak wavelengths broadens the contribution in the cyan-like region. As a result, a higher CRI (at slightly higher CCT) can be achieved while the drop in MDEF is small (FIG. 6). An even higher MDEF (and CRI>80) can be achieved by going to a slightly higher CCT. Starting with a higher CRI white LED does not prevent the CRI drop (CRI of the white+cyan combination in FIG. 6 is almost equal for a CRI 80 LED (cubes in FIG. 6) and CRI 90 LED (triangles in FIG. 6).

FIG. 6 depicts MDEF as a function of CRI for the combination of a 3000 K LED (CRI 80 LED cubes; CRI 90 LED triangles) and cyan LEDs. The labels indicates the peak wavelength difference, in nanometers, between the cyan LEDs used (0=single peak), see e.g. also FIG. 2F, wherein the peak wavelength difference is the difference between λmax2 and λmax3. The filling of the symbols indicate the color temperature of the combination of 3000 K LED and cyan LEDs, with the open symbols (CRIs of about over 80) being about 4000 K, with the hatched symbols (CRIs of about 73-82) being about 4500 K, and with the closed symbols (CRIs of about 67-72) 5000 K.

Hence, amongst others with the present invention a range can be covered of about the range defined by CRI;MDEF as x;y coordinates of the area defined by (65;1.2), (70;1.3), (85;0.7) and (90;0.8), more especially defined by (65;1.2), (67,5;1.25), (85;0.7) and (90;0.8).

Figure 7:
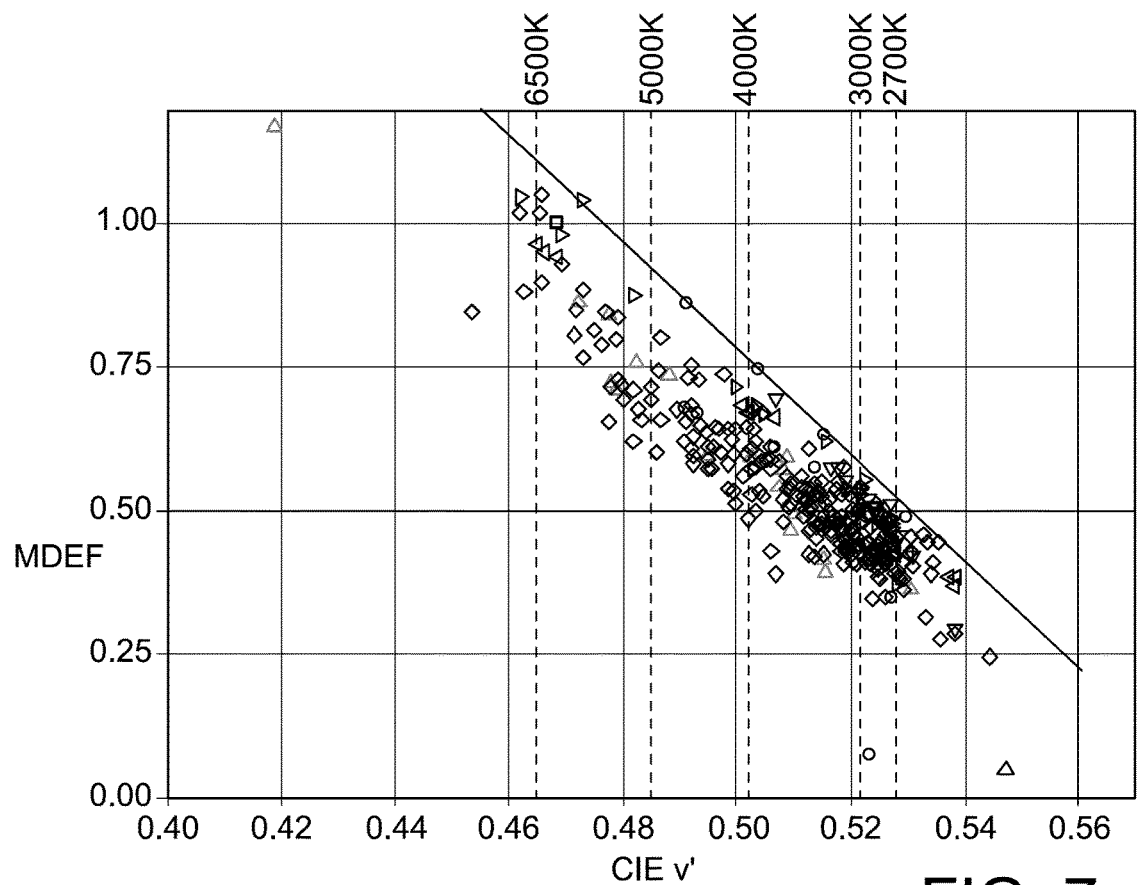
FIG. 7 shows the MDEF value as a function of CIE v' for different light sources. Vertical lines indicate the CIE v' of the BBL at different CCTs; the correlated color temperatures are indicated at the top of the Figure.

FIG. 7 shows the MDEF value as a function of CIE v' for different light sources. Vertical lines indicate the CIE v' of the BBL at different CCTs; the correlated color temperatures are indicated at the top of the Figure. Note that the area above the line cannot be addressed with state of the art light sources. However, the present invention can address this region. The line is defined as: MDEF>5.45-9.31*CIE v'.

Examples according to the present invention e.g. were:

in the region of the spectrum of the test spectrum (by weighing the spectrum with m(lambda). One can also calculate how many Lm are generated. The ratio of power in mW and lumen in Lm is called MELR value. For a D65 reference spectrum this calculation can also be done. The MELR of D65=1.326 mW/Lm. The ratio of the MELR value of the test spectrum to be evaluated and the MELR value of the reference spectrum (D65) is called MDEF (or MDEF value). MDEF is a value without units.

MELR can thus be expressed in mW/Lm in which the mW is calculated by $\Sigma_{\lambda=380}^{780} SPD(\lambda)m(\lambda)\Delta\lambda$. The lumens in Lm are calculated in the normal way.

As discussed above, especially the MDEF>5.43-9.31*CIE v'. Further, MELR value=1.326*MDEF value. Here, the values without units are applied. For instance, when the MELR is 1.326 mW/Lm, for the sake of definition, the MELR value is 1.326. Therefore, MELR value>7.22-12.3451*CIE v'. The MELR value may also be defined as MELF/(mw/Lm).

Figure 8:
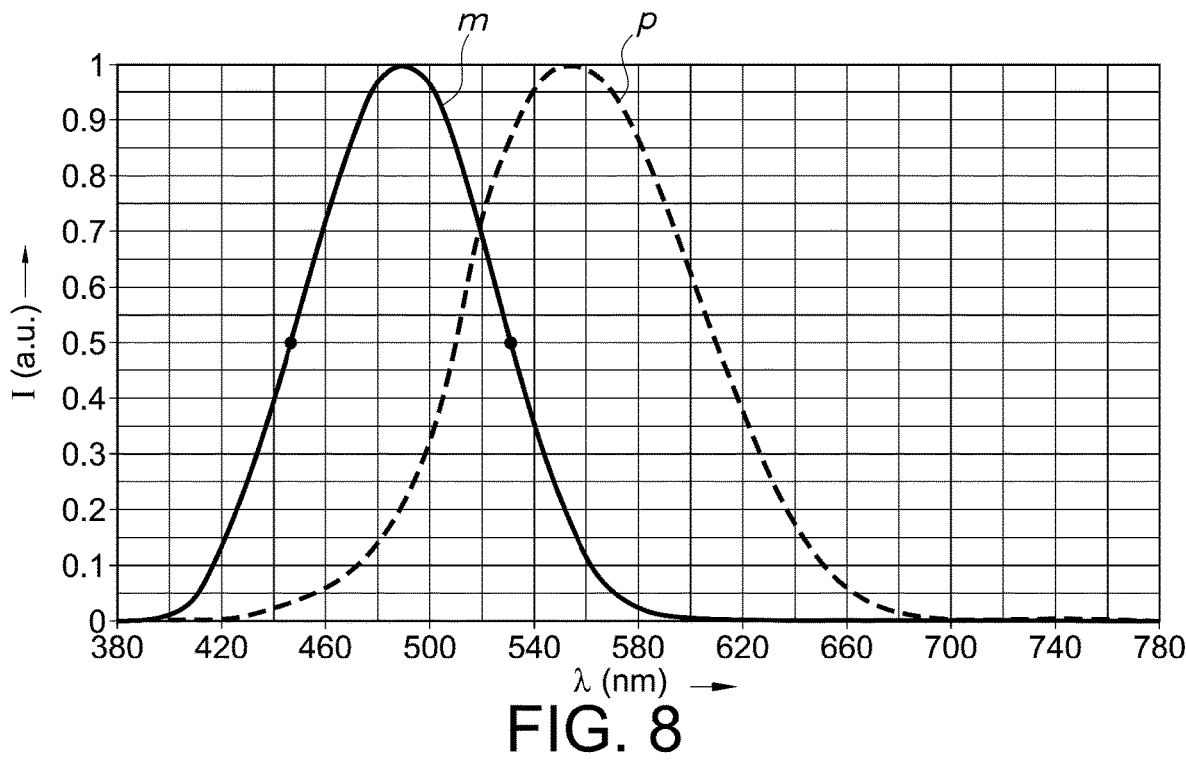
FIG. 8 shows the relative melanopic (m) (i.e. m($\lambda$)) and photopic (p) human eye sensitivity functions.

FIG. 8 shows the relative melanopic (m) (i.e. $m(\lambda)$) and photopic ($p(\lambda)$) human eye sensitivity functions. The maximum sensitivity for the melanopic function is at 490 nm, the full width half maximum values are at 447 nm and 531 nm, see also the accompanying table for the melanopic and photopic human eye sensitivity functions:

| | CIE v' | MELR | MDEF | Cyan-like (470-520 nm) contribution | Type |
|---|---|---|---|---|---|
| 1 | 0.5015 | 1.102 | 0.832 | 0.240 | white LED with cyan-like phosphor |
| 2 | 0.4925 | 1.224 | 0.924 | 0.257 | white LED with cyan-like phosphor |
| 3 | 0.4845 | 1.330 | 1.004 | 0.270 | white LED with cyan-like phosphor |
| 4 | 0.497 | 1.130 | 0.853 | 0.238 | white LED with cyan-like phosphor |
| 5 | 0.4789 | 1.334 | 1.006 | 0.257 | white LED with cyan-like phosphor |
| 6 | 0.5015 | 1.150 | 0.868 | 0.259 | White LED (3000 K; CRI 80) + cyan LED |
| 7 | 0.5015 | 1.142 | 0.862 | 0.256 | White LED (3000 K; CRI 80) + 2 different cyan LEDs |
| 8 | 0.5015 | 1.110 | 0.838 | 0.242 | White LED (3000 K; CRI 80) + 2 different cyan LEDs |
| 9 | 0.5015 | 1.059 | 0.800 | 0.225 | White LED (3000 K; CRI 80) + 2 different cyan LEDs |
| 10 | 0.4925 | 1.449 | 1.093 | 0.326 | White LED (2700 K; CRI 80) + cyan LED |
| 11 | 0.4925 | 1.430 | 1.080 | 0.320 | White LED (2700 K; CRI 80) + 2 different cyan LEDs |
| 12 | 0.4925 | 1.376 | 1.039 | 0.300 | White LED (2700 K; CRI 80) + 2 different cyan LEDs |
| 13 | 0.4925 | 1.277 | 0.964 | 0.266 | White LED (2700 K; CRI 80) + 2 different cyan LEDs |

Embodiments of white LED with cyan-like phosphor can be provided as LED with blend of luminescent materials, including the cyan-like phosphor, or can be provided as white LED with cyan-like LED.

Based on the experiments, it appears that even values of MDEF>1.25 can be achieved.

Instead of the MDEF value, also a MELR value (Melanopic efficacy of luminous radiation) may be used. With respect to the calculation of the MDEF value and the MELR value the following can be mentioned. For the test spectrum that is to be evaluated one may calculate how many mW are

| | Photopic | Melanopic |
|---|---|---|
| 380 | 0.000039 | 0.000918 |
| 381 | 4.28264E-05 | 0.001033 |
| 382 | 4.69146E-05 | 0.001163 |
| 383 | 5.15896E-05 | 0.00131 |
| 384 | 5.71764E-05 | 0.001477 |
| 385 | 0.000064 | 0.001667 |
| 386 | 7.23442E-05 | 0.001883 |
| 387 | 8.22122E-05 | 0.002129 |
| 388 | 9.35082E-05 | 0.00241 |
| 389 | 0.000106136 | 0.002729 |

|  | Photopic | Melanopic |
|---|---|---|
| 390 | 0.00012 | 0.003094 |
| 391 | 0.000134984 | 0.003512 |
| 392 | 0.000151492 | 0.003989 |
| 393 | 0.000170208 | 0.004536 |
| 394 | 0.000191816 | 0.005162 |
| 395 | 0.000217 | 0.00588 |
| 396 | 0.000246907 | 0.006705 |
| 397 | 0.00028124 | 0.007651 |
| 398 | 0.00031852 | 0.008739 |
| 399 | 0.000357267 | 0.009989 |
| 400 | 0.000396 | 0.011428 |
| 401 | 0.000433715 | 0.013104 |
| 402 | 0.000473024 | 0.015038 |
| 403 | 0.000517876 | 0.017268 |
| 404 | 0.000572219 | 0.019841 |
| 405 | 0.00064 | 0.022811 |
| 406 | 0.00072456 | 0.02624 |
| 407 | 0.0008255 | 0.0302 |
| 408 | 0.00094116 | 0.034773 |
| 409 | 0.00106988 | 0.040055 |
| 410 | 0.00121 | 0.046155 |
| 411 | 0.001362091 | 0.051431 |
| 412 | 0.001530752 | 0.057325 |
| 413 | 0.001720368 | 0.06391 |
| 414 | 0.001935323 | 0.071264 |
| 415 | 0.00218 | 0.079477 |
| 416 | 0.0024548 | 0.088645 |
| 417 | 0.002764 | 0.098878 |
| 418 | 0.0031178 | 0.110297 |
| 419 | 0.0035264 | 0.123034 |
| 420 | 0.004 | 0.137237 |
| 421 | 0.00454624 | 0.146047 |
| 422 | 0.00515932 | 0.155409 |
| 423 | 0.00582928 | 0.16535 |
| 424 | 0.00654616 | 0.175902 |
| 425 | 0.0073 | 0.187096 |
| 426 | 0.008086507 | 0.198964 |
| 427 | 0.00890872 | 0.21154 |
| 428 | 0.00976768 | 0.224858 |
| 429 | 0.01066443 | 0.238954 |
| 430 | 0.0116 | 0.253865 |
| 431 | 0.01257317 | 0.266176 |
| 432 | 0.01358272 | 0.279 |
| 433 | 0.01462968 | 0.29235 |
| 434 | 0.01571509 | 0.306239 |
| 435 | 0.01684 | 0.320679 |
| 436 | 0.01800736 | 0.335684 |
| 437 | 0.01921448 | 0.351265 |
| 438 | 0.02045392 | 0.367435 |
| 439 | 0.02171824 | 0.384205 |
| 440 | 0.023 | 0.401587 |
| 441 | 0.02429461 | 0.415459 |
| 442 | 0.02561024 | 0.429639 |
| 443 | 0.02695857 | 0.444126 |
| 444 | 0.02835125 | 0.458915 |
| 445 | 0.0298 | 0.474003 |
| 446 | 0.03131083 | 0.489382 |
| 447 | 0.03288368 | 0.505051 |
| 448 | 0.03452112 | 0.520999 |
| 449 | 0.03622571 | 0.537223 |
| 450 | 0.038 | 0.553715 |
| 451 | 0.03984667 | 0.56863 |
| 452 | 0.041768 | 0.583694 |
| 453 | 0.043766 | 0.598893 |
| 454 | 0.04584267 | 0.614217 |
| 455 | 0.048 | 0.629654 |
| 456 | 0.05024368 | 0.645191 |
| 457 | 0.05257304 | 0.660812 |
| 458 | 0.05498056 | 0.676507 |
| 459 | 0.05745872 | 0.692256 |
| 460 | 0.06 | 0.708048 |
| 461 | 0.06260197 | 0.723532 |
| 462 | 0.06527752 | 0.739008 |
| 463 | 0.06804208 | 0.75446 |
| 464 | 0.07091109 | 0.769869 |
| 465 | 0.0739 | 0.785216 |
| 466 | 0.077016 | 0.800481 |
| 467 | 0.0802664 | 0.815643 |
| 468 | 0.0836668 | 0.830679 |
| 469 | 0.0872328 | 0.845571 |
| 470 | 0.09098 | 0.86029 |
| 471 | 0.09491755 | 0.872405 |
| 472 | 0.09904584 | 0.88423 |
| 473 | 0.1033674 | 0.89574 |
| 474 | 0.1078846 | 0.906916 |
| 475 | 0.1126 | 0.917734 |
| 476 | 0.117532 | 0.928169 |
| 477 | 0.1226744 | 0.938197 |
| 478 | 0.1279928 | 0.947794 |
| 479 | 0.1334528 | 0.956938 |
| 480 | 0.13902 | 0.965604 |
| 481 | 0.1446764 | 0.971753 |
| 482 | 0.1504693 | 0.977347 |
| 483 | 0.1564619 | 0.98237 |
| 484 | 0.1627177 | 0.9868 |
| 485 | 0.1693 | 0.990622 |
| 486 | 0.1762431 | 0.993814 |
| 487 | 0.1835581 | 0.996364 |
| 488 | 0.1912735 | 0.998254 |
| 489 | 0.199418 | 0.999471 |
| 490 | 0.20802 | 1 |
| 491 | 0.2171199 | 0.999832 |
| 492 | 0.2267345 | 0.998957 |
| 493 | 0.2368571 | 0.997369 |
| 494 | 0.2474812 | 0.995059 |
| 495 | 0.2586 | 0.992021 |
| 496 | 0.2701849 | 0.988257 |
| 497 | 0.2822939 | 0.983766 |
| 498 | 0.2950505 | 0.978548 |
| 499 | 0.308578 | 0.972608 |
| 500 | 0.323 | 0.965951 |
| 501 | 0.3384021 | 0.958588 |
| 502 | 0.3546858 | 0.950526 |
| 503 | 0.3716986 | 0.941781 |
| 504 | 0.3892875 | 0.932367 |
| 505 | 0.4073 | 0.9223 |
| 506 | 0.4256299 | 0.911597 |
| 507 | 0.4443096 | 0.900281 |
| 508 | 0.4633944 | 0.888376 |
| 509 | 0.4829395 | 0.875903 |
| 510 | 0.503 | 0.862887 |
| 511 | 0.5235693 | 0.848186 |
| 512 | 0.544512 | 0.833038 |
| 513 | 0.56569 | 0.817476 |
| 514 | 0.5869653 | 0.80153 |
| 515 | 0.6082 | 0.785234 |
| 516 | 0.6293456 | 0.768617 |
| 517 | 0.6503068 | 0.751716 |
| 518 | 0.6708752 | 0.734563 |
| 519 | 0.6908424 | 0.71719 |
| 520 | 0.71 | 0.699628 |
| 521 | 0.7281852 | 0.681754 |
| 522 | 0.7454636 | 0.663768 |
| 523 | 0.7619694 | 0.645696 |
| 524 | 0.7778368 | 0.62757 |
| 525 | 0.7932 | 0.609422 |
| 526 | 0.8081104 | 0.59128 |
| 527 | 0.8224962 | 0.573171 |
| 528 | 0.8363068 | 0.555121 |
| 529 | 0.8494916 | 0.537159 |
| 530 | 0.862 | 0.519309 |
| 531 | 0.8738108 | 0.501594 |
| 532 | 0.8849624 | 0.484037 |
| 533 | 0.8954936 | 0.466662 |
| 534 | 0.9054432 | 0.449487 |
| 535 | 0.9148501 | 0.432534 |
| 536 | 0.9237348 | 0.41582 |
| 537 | 0.9320924 | 0.399364 |
| 538 | 0.9399226 | 0.383183 |
| 539 | 0.9472252 | 0.367292 |
| 540 | 0.954 | 0.351707 |
| 541 | 0.9602561 | 0.336519 |
| 542 | 0.9660074 | 0.321656 |
| 543 | 0.9712606 | 0.30713 |

-continued

|     | Photopic  | Melanopic |
|-----|-----------|-----------|
| 544 | 0.9760225 | 0.292953  |
| 545 | 0.9803    | 0.279135  |
| 546 | 0.9840924 | 0.265686  |
| 547 | 0.9874182 | 0.252613  |
| 548 | 0.9903128 | 0.239924  |
| 549 | 0.9928116 | 0.227626  |
| 550 | 0.9949501 | 0.215722  |
| 551 | 0.9967108 | 0.204171  |
| 552 | 0.9980983 | 0.193028  |
| 553 | 0.999112  | 0.182295  |
| 554 | 0.9997482 | 0.171971  |
| 555 | 1         | 0.162056  |
| 556 | 0.9998567 | 0.152549  |
| 557 | 0.9993046 | 0.143447  |
| 558 | 0.9983255 | 0.134745  |
| 559 | 0.9968987 | 0.12644   |
| 560 | 0.995     | 0.118526  |
| 561 | 0.9926005 | 0.110943  |
| 562 | 0.9897426 | 0.103744  |
| 563 | 0.9864444 | 0.096917  |
| 564 | 0.9827241 | 0.090455  |
| 565 | 0.9786    | 0.084346  |
| 566 | 0.9740837 | 0.078579  |
| 567 | 0.9691712 | 0.073143  |
| 568 | 0.9638568 | 0.068026  |
| 569 | 0.9581349 | 0.063217  |
| 570 | 0.952     | 0.058701  |
| 571 | 0.9454504 | 0.054443  |
| 572 | 0.9384992 | 0.050457  |
| 573 | 0.9311628 | 0.046732  |
| 574 | 0.9234576 | 0.043253  |
| 575 | 0.9154    | 0.040009  |
| 576 | 0.9070064 | 0.036986  |
| 577 | 0.8982772 | 0.034174  |
| 578 | 0.8892048 | 0.031558  |
| 579 | 0.8797816 | 0.029129  |
| 580 | 0.87      | 0.026875  |
| 581 | 0.8598613 | 0.024784  |
| 582 | 0.849392  | 0.022848  |
| 583 | 0.838622  | 0.021055  |
| 584 | 0.8275813 | 0.019396  |
| 585 | 0.8163    | 0.017862  |
| 586 | 0.8047947 | 0.016446  |
| 587 | 0.793082  | 0.015137  |
| 588 | 0.781192  | 0.01393   |
| 589 | 0.7691547 | 0.012817  |
| 590 | 0.757     | 0.01179   |
| 591 | 0.7447541 | 0.010839  |
| 592 | 0.7324224 | 0.009964  |
| 593 | 0.7200036 | 0.009158  |
| 594 | 0.7074965 | 0.008416  |
| 595 | 0.6949    | 0.007734  |
| 596 | 0.6822192 | 0.007107  |
| 597 | 0.6694716 | 0.006531  |
| 598 | 0.6566744 | 0.006001  |
| 599 | 0.6438448 | 0.005514  |
| 600 | 0.631     | 0.005067  |
| 601 | 0.6181555 | 0.004655  |
| 602 | 0.6053144 | 0.004277  |
| 603 | 0.5924756 | 0.003929  |
| 604 | 0.5796379 | 0.00361   |
| 605 | 0.5668    | 0.003318  |
| 606 | 0.5539611 | 0.003049  |
| 607 | 0.5411372 | 0.002802  |
| 608 | 0.5283528 | 0.002576  |
| 609 | 0.5156323 | 0.002368  |
| 610 | 0.503     | 0.002177  |
| 611 | 0.4904688 | 0.002002  |
| 612 | 0.4780304 | 0.001841  |
| 613 | 0.4656776 | 0.001693  |
| 614 | 0.4534032 | 0.001558  |
| 615 | 0.4412    | 0.001433  |
| 616 | 0.42908   | 0.001319  |
| 617 | 0.417036  | 0.001214  |
| 618 | 0.405032  | 0.001117  |
| 619 | 0.393032  | 0.001029  |
| 620 | 0.381     | 0.000947  |

-continued

|     | Photopic   | Melanopic |
|-----|------------|-----------|
| 621 | 0.3689184  | 0.000872  |
| 622 | 0.3568272  | 0.000803  |
| 623 | 0.3447768  | 0.00074   |
| 624 | 0.3328176  | 0.000681  |
| 625 | 0.321      | 0.000628  |
| 626 | 0.3093381  | 0.000578  |
| 627 | 0.2978504  | 0.000533  |
| 628 | 0.2865936  | 0.000491  |
| 629 | 0.2756245  | 0.000453  |
| 630 | 0.265      | 0.000418  |
| 631 | 0.2547632  | 0.000386  |
| 632 | 0.2448896  | 0.000356  |
| 633 | 0.2353344  | 0.000328  |
| 634 | 0.2260528  | 0.000303  |
| 635 | 0.217      | 0.00028   |
| 636 | 0.2081616  | 0.000258  |
| 637 | 0.1995488  | 0.000239  |
| 638 | 0.1911552  | 0.000221  |
| 639 | 0.1829744  | 0.000204  |
| 640 | 0.175      | 0.000188  |
| 641 | 0.1672235  | 0.000174  |
| 642 | 0.1596464  | 0.000161  |
| 643 | 0.1522776  | 0.000149  |
| 644 | 0.1451259  | 0.000138  |
| 645 | 0.1382     | 0.000127  |
| 646 | 0.1315003  | 0.000118  |
| 647 | 0.1250248  | 0.000109  |
| 648 | 0.1187792  | 0.000101  |
| 649 | 0.1127691  | 0.000093  |
| 650 | 0.107      | 0.000087  |
| 651 | 0.1014762  | 0.00008   |
| 652 | 0.09618864 | 0.000074  |
| 653 | 0.09112296 | 0.000069  |
| 654 | 0.08626485 | 0.000064  |
| 655 | 0.0816     | 0.000059  |
| 656 | 0.07712064 | 0.000055  |
| 657 | 0.07282552 | 0.000051  |
| 658 | 0.06871008 | 0.000047  |
| 659 | 0.06476976 | 0.000044  |
| 660 | 0.061      | 0.000041  |
| 661 | 0.05739621 | 0.000038  |
| 662 | 0.05395504 | 0.000035  |
| 663 | 0.05067376 | 0.000033  |
| 664 | 0.04754965 | 0.00003   |
| 665 | 0.04458    | 0.000028  |
| 666 | 0.04175872 | 0.000026  |
| 667 | 0.03908496 | 0.000024  |
| 668 | 0.03656384 | 0.000023  |
| 669 | 0.03420048 | 0.000021  |
| 670 | 0.032      | 0.00002   |
| 671 | 0.02996261 | 0.000018  |
| 672 | 0.02807664 | 0.000017  |
| 673 | 0.02632626 | 0.000016  |
| 674 | 0.02470805 | 0.000015  |
| 675 | 0.0232     | 0.000014  |
| 676 | 0.02180077 | 0.000013  |
| 677 | 0.02050112 | 0.000012  |
| 678 | 0.01928108 | 0.000011  |
| 679 | 0.01812069 | 0.00001   |
| 680 | 0.017      | 0.00001   |
| 681 | 0.01590379 | 0.000009  |
| 682 | 0.01483718 | 0.000008  |
| 683 | 0.01381068 | 0.000008  |
| 684 | 0.01283478 | 0.000007  |
| 685 | 0.01192    | 0.000007  |
| 686 | 0.01106831 | 0.000006  |
| 687 | 0.01027339 | 0.000006  |
| 688 | 0.009533311| 0.000005  |
| 689 | 0.008846157| 0.000005  |
| 690 | 0.00821    | 0.000005  |
| 691 | 0.007623781| 0.000004  |
| 692 | 0.007085424| 0.000004  |
| 693 | 0.006591476| 0.000004  |
| 694 | 0.006138485| 0.000004  |
| 695 | 0.005723   | 0.000003  |
| 696 | 0.005343059| 0.000003  |
| 697 | 0.004995796| 0.000003  |

| | Photopic | Melanopic |
|---|---|---|
| 698 | 0.004676404 | 0.000003 |
| 699 | 0.004380075 | 0.000003 |
| 700 | 0.004102 | 0.000002 |
| 701 | 0.003838453 | 0.000002 |
| 702 | 0.003589099 | 0.000002 |
| 703 | 0.003354219 | 0.000002 |
| 704 | 0.003134093 | 0.000002 |
| 705 | 0.002929 | 0.000002 |
| 706 | 0.002738139 | 0.000002 |
| 707 | 0.002559876 | 0.000002 |
| 708 | 0.002393244 | 0.000001 |
| 709 | 0.002237275 | 0.000001 |
| 710 | 0.002091 | 0.000001 |
| 711 | 0.001953587 | 0.000001 |
| 712 | 0.00182458 | 0.000001 |
| 713 | 0.00170358 | 0.000001 |
| 714 | 0.001590187 | 0.000001 |
| 715 | 0.001484 | 0.000001 |
| 716 | 0.001384496 | 0.000001 |
| 717 | 0.001291268 | 0.000001 |
| 718 | 0.001204092 | 0.000001 |
| 719 | 0.001122744 | 0.000001 |
| 720 | 0.001047 | 0.000001 |
| 721 | 0.00097659 | 0.000001 |
| 722 | 0.000911109 | 0.000001 |
| 723 | 0.000850133 | 0.000001 |
| 724 | 0.000793238 | 0.000001 |
| 725 | 0.00074 | 0 |
| 726 | 0.000690083 | 0 |
| 727 | 0.00064331 | 0 |
| 728 | 0.000599496 | 0 |
| 729 | 0.000558455 | 0 |
| 730 | 0.00052 | 0 |
| 731 | 0.000483914 | 0 |
| 732 | 0.000450053 | 0 |
| 733 | 0.000418345 | 0 |
| 734 | 0.000388718 | 0 |
| 735 | 0.0003611 | 0 |
| 736 | 0.000335384 | 0 |
| 737 | 0.00031144 | 0 |
| 738 | 0.000289166 | 0 |
| 739 | 0.000268454 | 0 |
| 740 | 0.0002492 | 0 |
| 741 | 0.000231302 | 0 |
| 742 | 0.000214686 | 0 |
| 743 | 0.000199288 | 0 |
| 744 | 0.000185048 | 0 |
| 745 | 0.0001719 | 0 |
| 746 | 0.000159778 | 0 |
| 747 | 0.000148604 | 0 |
| 748 | 0.000138302 | 0 |
| 749 | 0.000128793 | 0 |
| 750 | 0.00012 | 0 |
| 751 | 0.00011186 | 0 |
| 752 | 0.000104322 | 0 |
| 753 | 9.73356E−05 | 0 |
| 754 | 9.08459E−05 | 0 |
| 755 | 0.0000848 | 0 |
| 756 | 7.91467E−05 | 0 |
| 757 | 0.000073858 | 0 |
| 758 | 0.000068916 | 0 |
| 759 | 6.43027E−05 | 0 |
| 760 | 0.00006 | 0 |
| 761 | 5.59819E−05 | 0 |
| 762 | 5.22256E−05 | 0 |
| 763 | 4.87184E−05 | 0 |
| 764 | 4.54475E−05 | 0 |
| 765 | 0.0000424 | 0 |
| 766 | 3.9561E−05 | 0 |
| 767 | 3.69151E−05 | 0 |
| 768 | 3.44487E−05 | 0 |
| 769 | 3.21482E−05 | 0 |
| 770 | 0.00003 | 0 |
| 771 | 2.79913E−05 | 0 |
| 772 | 2.61136E−05 | 0 |
| 773 | 2.43602E−05 | 0 |
| 774 | 2.27246E−05 | 0 |
| 775 | 0.0000212 | 0 |
| 776 | 1.97789E−05 | 0 |
| 777 | 1.84529E−05 | 0 |
| 778 | 1.72169E−05 | 0 |
| 779 | 1.60646E−05 | 0 |
| 780 | 0.00001499 | 0 |

Figure 9:
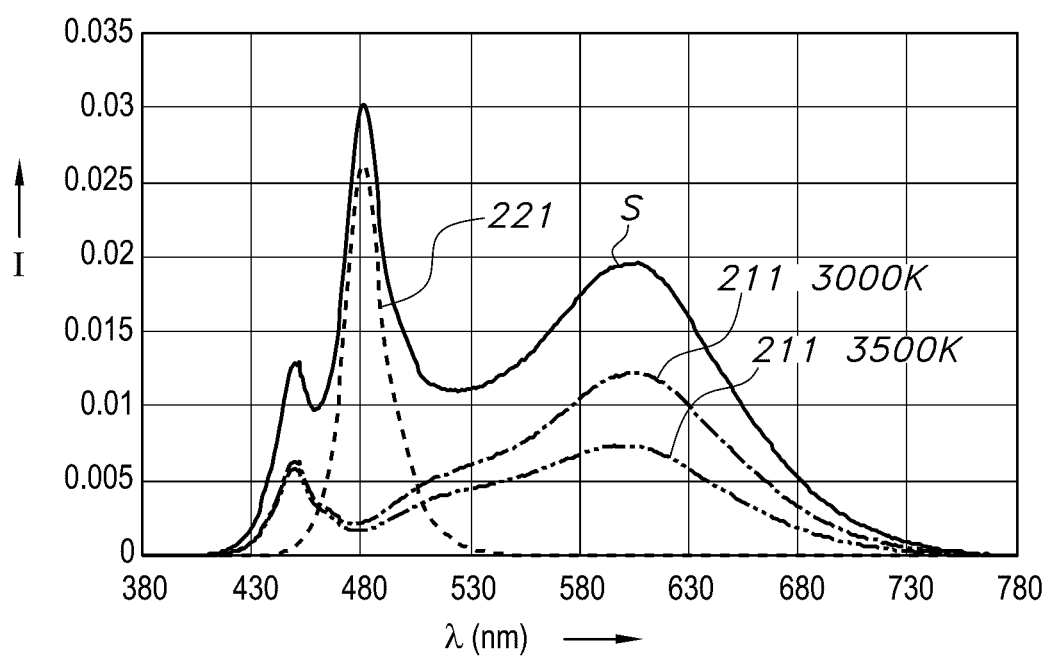
FIG. 9 shows spectral distributions of further embodiments.

Neutral white light with a very high MDEF while maintaining good color quality i.e. white appearance, CRI>80 and R9>50, can e.g. be achieved by combining direct cyan LEDs with a dominant wavelength (DWL) of e.g. about 482 nm with CRI 80 white LEDs with color point around BBL at ~3250K. Then the resulting color point of the light source lies below the BBL, which is desirable to obtain white appearance. In FIG. 9 the individual LED and sum color points are shown, and the sum spectrum is given.

Reference 211 3000 K indicates the correlated color temperature of 3000 K of an example of first light 211 and reference 211 3500 K indicates the correlated color temperature of 3500 K of another first light 211. Together they provide a correlated color temperature of about 3250 K. References 221 indicates second light 221 (with the two different white contributions having CCT of 3000 K and 3500 K, respectively). S indicates the sum of the first light 211 and the second light 221.

To achieve this spectrum, the optical power from the cyan LEDs needs to be about ~0.65 Wopt per 1100 lm white. Using state-of-the-art LEDs, this can be achieved using cyan and ~3250K CRI80 white LEDs in a ratio of about 1:4 in series in the same string. To meet total flux output needed and proper string voltage to match the driver, several groups of (1 cyan+4 white) LEDs can be placed in series, and several equal strings can be placed in parallel.

Figure 10:
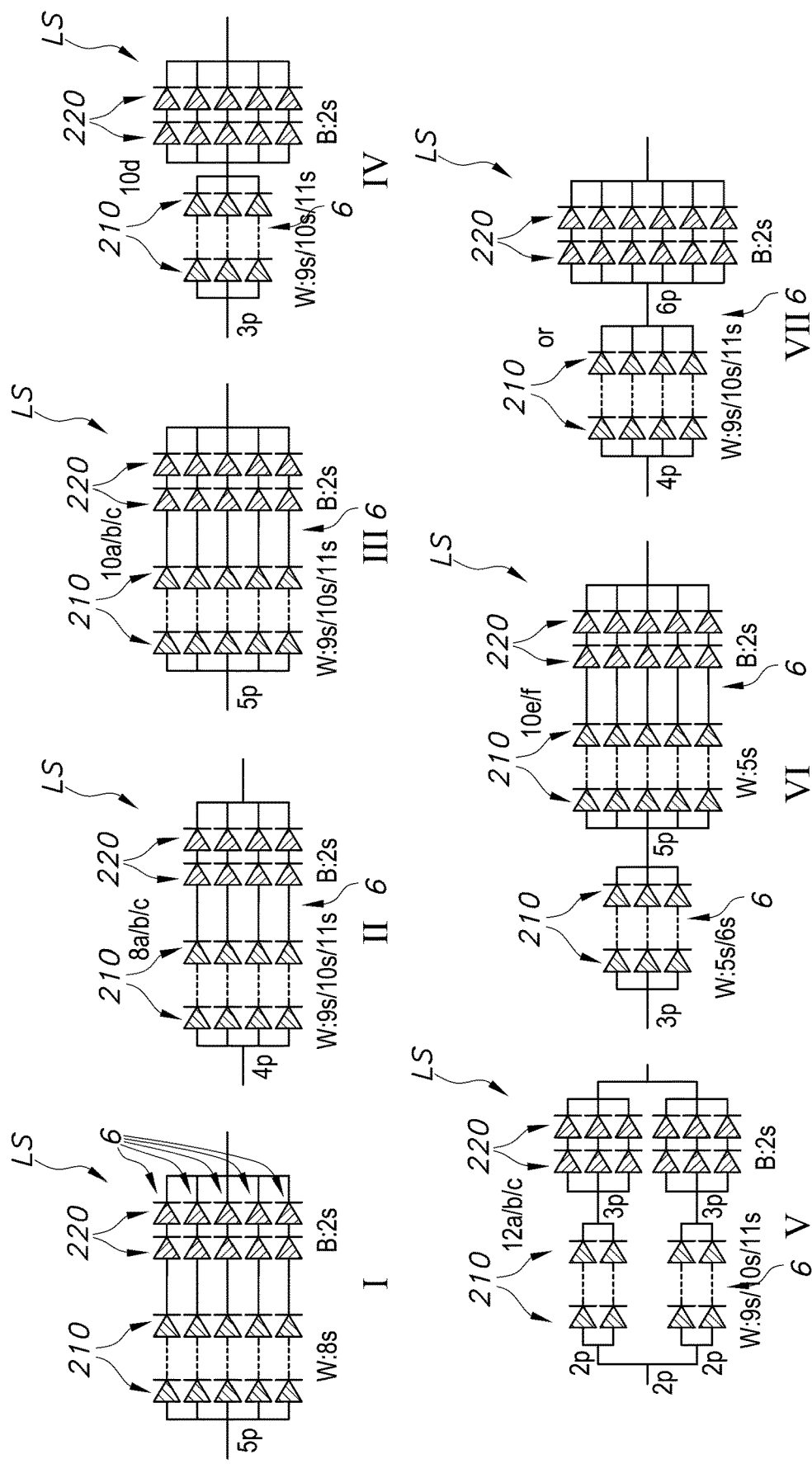
FIG. 10 schematically depict some possible string configurations.

An example string configuration is given in FIG. 10, example i. Here, a LED string LS is schematically depicted with 5 groups of subsets of each k=10 LEDs, wherein the 10 LEDs are configured in series, wherein all n=5 groups of subsets of k LEDs are configured in parallel in the LED string. Note, each group comprises 8 first sources 210 and 2 second sources 220.

In case the flux ratio of the cyan and white LEDs is different, then a different ratio of cyan to white LEDs can be applied to still meet the requirement of ~0.65 Wopt cyan light per 1100 lm white.

If a different ratio of LEDs is preferred, but still ~0.65 Wopt cyan light per 1100 lm white is needed, the cyan and white LEDs can both be placed in parallel strings, where the number of parallel strings for cyan and white is unequal. See FIG. 10ii-10vii for various options. In case of linear modules for office, the cyan LEDs are preferably equally spaced apart with a constant number of white LEDs in between, in order to have a uniform light distribution. In that case, options 8b, 10b, 10d, 10e and 12a remain, i.e. have an integer ratio of white to cyan LEDs. But in other cases, where the LEDs are not spatially far apart, e.g. in bulbs or downlights, all options in FIG. 10 are possible.

For instance, the LED string LS in embodiment iv includes a set of three parallel arranged groups (of each e.g. 10 first sources 210) configured in series with a second set of five parallel arranged groups (of each e.g. 2 second sources 220). Further, for instance the embodiment of vi in FIG. 10 shows two sets configured in series, with a first set comprising three parallel arranged groups of each e.g. 5 or first sources 210, and with a second set with 5 parallel arranged groups, with each e.g. 5 first sources 210 and 2 second sources 220.

If the optical requirements are different, e.g. CRI 90 is required instead of CRI 80, or a CCT different from 4200K is required, then the cyan flux per 1100 lm white will be different (lower) from 0.65 Wopt. Then the cyan to white LED ratio and/or string configuration can be adapted accordingly to meet the spec. For example, if 4200K CRI90 is required, cyan flux per 1100 lm white needs to be 0.30 Wopt, which can be achieved with 1:8 cyan & white LEDs in series. In this case some of the solutions in FIG. 10 might be more preferred, otherwise the white LED count becomes too high. Starting with (standard) CRI 80 white LEDs it may not easily be possible to obtain a R9>50 at the target color point.

Further, it appears that the dominant wavelength of the cyan LED that needs to be combined with the white LED (in order to stay close to, but slightly below BBL) may depend on the CCT of the white LED: DWL close to 490 nm for 2200 K, close to 485 nm for 3000 K and close to 477 nm for the neutral white LEDs (4000 K).

Figure 11:
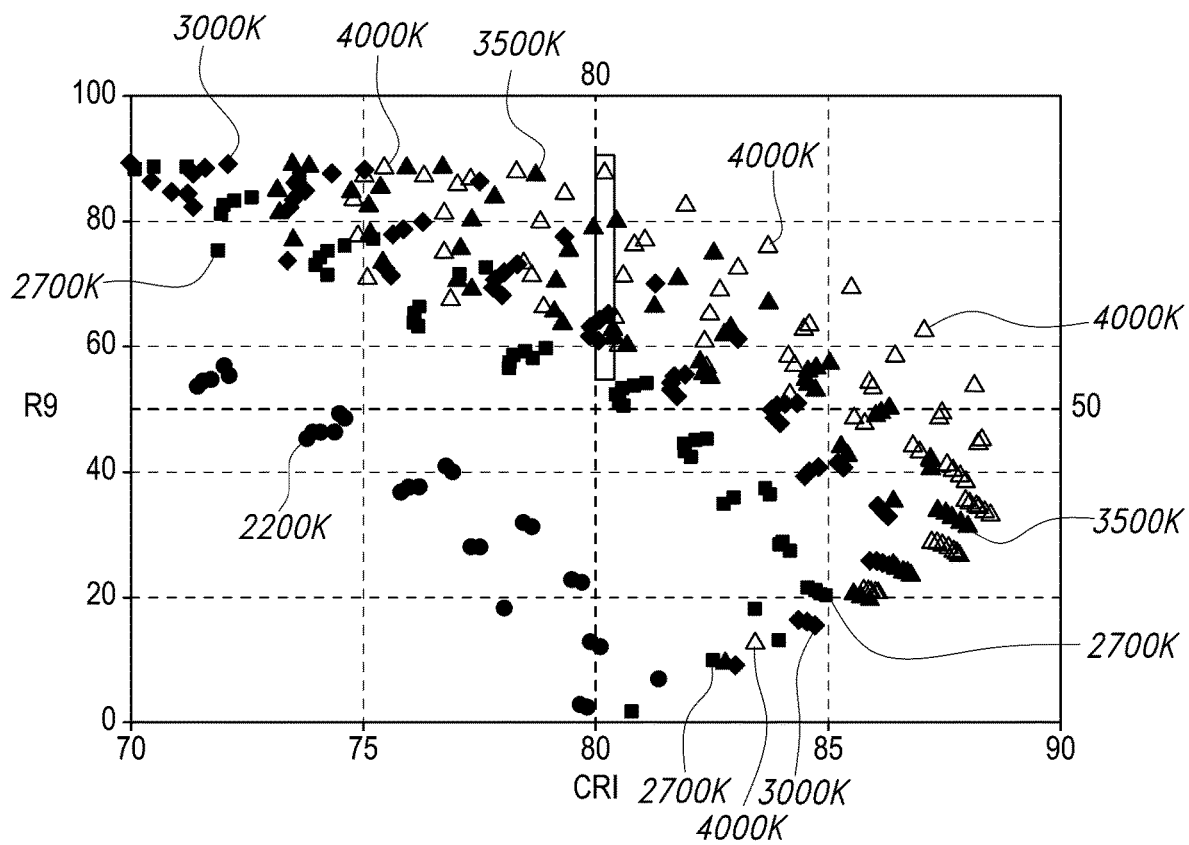
FIG. 11 shows R9 as function of CRI starting with different correlated color temperatures as first light 211; the contribution of second light varies (increases from 0, starting from the point near 80, 0)

Adding a small amount of cyan light will lead to an increase in CRI and R9 (FIG. 11), except for the case where we start with a 2200K LED (here CRI immediately decreases). In some cases, the CRI increases to a value close to 90. After the initial increase of CRI, CRI starts to decrease with increasing cyan content. For maximum MDEF, however, the cyan content in the spectrum should be as high as possible, but the application requirements (office lighting) require a minimum level of 80. So we want to end up close to the CRI 80 in the upper right section of FIG. 11 (the box). Advantageously, in this case R9 is >50, which will lead to one extra WELL point. FIG. 11 depicts the R9 value (y-axis) as function of CRI (x-axis) for the device light having a CRI of between 70 and 90 and were the first light (210) having a CCT of 2200 K (closed circles), 2700 K (closed square), 3000 K (closed diamonds), 3500 K (closed triangles), or 4000 K (open triangles) and further as function of adding cyan light. Hence, at no cyan light, all curves start at about CRI=80 and R9 is 0. For the first light with 2200 K, the effect of adding cyan light is an increase of R9 (like in all cases), but in a decrease of CRI. For all other curves, there is a part, in a counter clock wise direction, wherein the CRI first increases up to about 85-90, and then decreases, to return at about CRI=80, to further decrease when more cyan is added. The amount of cyan added to arrive again at a value of close to 80 or slightly larger, as indicated with the box, may be the best amount (highest MDER value possible), as a lower amount means a lower R9 and a higher amount means a lower CRI.

Figure 12:
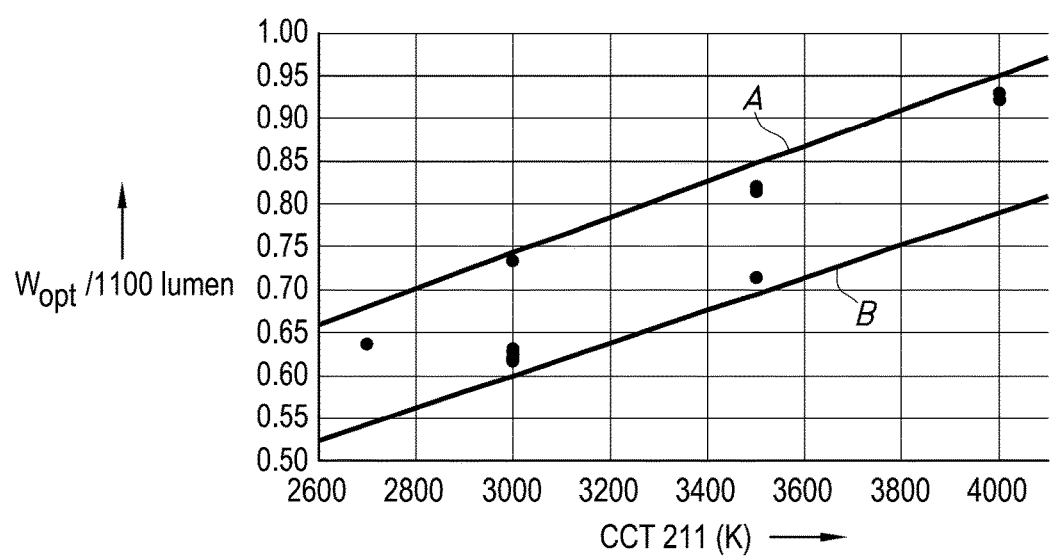
FIG. 12 shows embodiments of combinations of Wopt/1100 lm of the second light and correlated color temperatures of the first light 211 where all spectral requirements are met.

The amount of cyan flux (expressed as Wopt per 1100 Lm white device light) of the datapoints in the box of FIG. 11 is plotted in FIG. 12 as function of the CCT of the white LED. There is a clear trend: the higher the white LED CCT, the higher the relative cyan flux to reach highest MDEF while still meeting CRI>80 (and by R9>50). On the x-axis, the correlated color temperature in Kelvin is depicted of the white first light 211. On the y-axis the optical power of the cyan flux (per 1000 lm of the white device light) added. The addition of the cyan light seems to be defined by the two lines A and B, which are defined as:

A: Wopt=0.12+000208*CCT (with CCT being the CCT of the white first light in Kelvin and with Wopt being the power in Watts (per 1100 lumen of the white device light));

B: Wopt=0.03+0.00019*CCT (with CCT being the CCT of the white first light in Kelvin and with Wopt being the power in Watts (per 1100 lumen of the white device light)).

Hence, these boundaries can be used, especially between the CCT range of 2300-4500 K, such as 2500-4200 K (of the white first light component).

Figure 13:
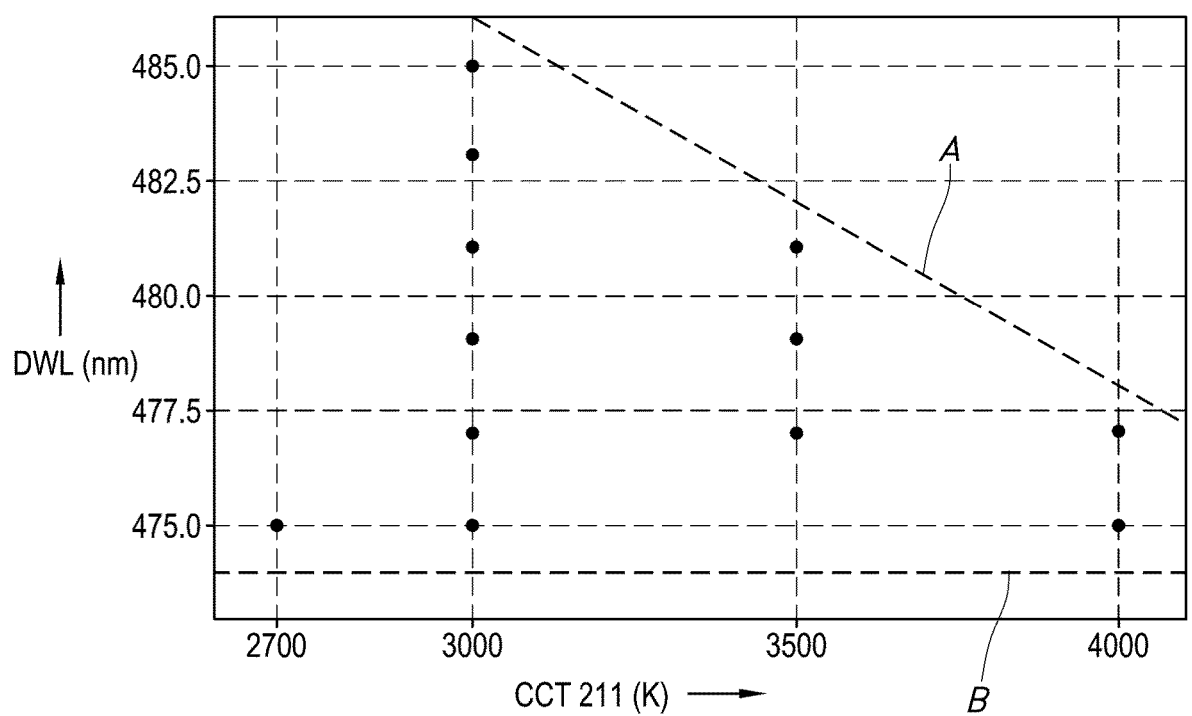
FIG. 13 shows embodiments of combinations of the dominant wavelength of the second light and correlated color temperature of the first light 211 where all spectral requirements are met.

FIG. 13 shows the dependence of the dominant wavelength of the second light (y-axis) as function of the correlated color temperature CCT of the first light 211 (x-axis). It appears that within the CCT range of about 2500-4200 K, especially about 2700-4000 K, the dominant wavelength range DWL in nanometer is defined by the formula: 474<DWL<(510-0.008*CCT). Here, DWL refers to the value of the dominant wavelength (in nm), 474 refers to the lower limit of 474 nm, and CCT refers to the value of the correlated color temperature of the first light. For instance, when the CCT is 3500 K, the formula is: 474<DWL<(510-0.008*3500, i.e. the dominant wavelength range DWL is between 474 nm and 482 nm. The dots in the graph are examples of possible dominant wavelengths at the indicate CCTs.

In another embodiment (see e.g. also FIGS. 2H and 2I), the second source of second light is a direct cyan chip that is placed in a package together with the blue chip and phosphor generating the first light. The phosphor may be covering both chips, as this improves color mixing and still the spectral performance (color point, CRI, R9, MDER) can be achieved by the right choice of chip dominant wavelengths and phosphors. The 2 chips can be placed in a single string, or can be in 2 strings making tuning of CCT and/or MDER possible. In embodiments, the blue first light source and the cyan second light source may be controllable, which allows control of the spectral power distribution of the device light.

The term "plurality" refers to two or more. The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%.

The term "comprise" includes also embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices, apparatus, or systems may herein amongst others be described during operation. As will be clear to the person skilled in the art, the invention is not limited to methods of operation, or devices, apparatus, or systems in operation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A light generating device configured to generate in a first control mode device light, wherein the light generating device comprises (i) a first source of first light, and (ii) a second source of second light, different from the first light, wherein the second light comprises cyan-like light having a wavelength selected from the range of 470-520 nm, wherein the device light comprises the first light and the second light, and wherein in the first control mode the device light is white light, and wherein the light generating device is configured to provide in the first control mode the device light having a MDEF (Melanopic D65 Efficiency Factor) value of ≥5.43-9.31*v', wherein v' refers to the color coordinates in the CIELUV color space; and wherein the MDEF is defined as:

$$MDEF = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda}$$

wherein SPD(λ) is the spectral power distribution of the light emitted by the light generating device (m λ) is the melanopic sensitivity function, the V(λ) is the photopic sensitivity function, and wherein the second light has a dominant wavelength selected from the range of 474-500 nm, wherein the first light has a correlated color temperature selected from the range of 2500-4500 K, and wherein the light generating device is configured to generate in the first control mode device light having a color point within 15 SDCM (Standard Deviation pf Color Matching) from the black body locus.

2. The light generating device according to claim 1, wherein in the first control mode the first light is white light, or cyan-depleted white light.

3. The light generating device according to claim 2, wherein the first source comprises a first light source configured to generate first light source light comprising the first light, and a first luminescent material configured to convert part of the first light source light into a first luminescent material light, wherein the second light comprises at least part of the first luminescent material light, and wherein in the first control mode the first light is cyan-depleted white light having a correlated color temperature of at maximum 3500 K and having a color point in the range of 15-30 SDCM below the black body locus.

4. The light generating device according to claim 3, wherein the light generating device further comprises a second luminescent material configured to convert part of the first light source light into second luminescent material light, and optionally one or more further luminescent materials configured to convert part of the first light source light into further luminescent material light, wherein the light generating device comprises a luminescent element comprising the first luminescent material, the second luminescent material, and the optional one or more further luminescent materials, and wherein the device light comprises the first light source light, the first luminescent material light, the second luminescent material light, and the optional further luminescent material light.

5. The light generating device according to claim 2, wherein the first source comprises a first light source configured to generate first light source light comprising the first light, wherein the second source comprises a second light source configured to generate second light source light, and (iii) a first luminescent material configured to convert at least part of the second light source light into a first luminescent material light, wherein the second light comprises at least part of the first luminescent material light and optionally unconverted second light source light.

6. The light generating device according to claim 5, wherein the second light has a color point (u';v') defined by the CIE u'v' area (0.03;0.22), (0.12;0.22), (0.03;0.55), and (0.12;0.55) in the CIE u'v' color space.

7. The light generating device according to claim 1, wherein the first light source comprises a first solid state light source, wherein the second light source comprises a second solid state light source, wherein the first solid state light source and the second solid state light source are configured in series in a LED string (LS).

8. The light generating device according to claim 3, wherein the first luminescent material comprises $ML_2O_2N_2$:$Eu^{2+}$, wherein M is selected from the group consisting of Ca, Sr and Ba, and wherein L is selected from the group consisting of Si and Ge, wherein M at least comprises Ba, and wherein L at least comprises Si.

9. The light generating device according to claim 5, wherein the first light source is configured to generate blue first light source light, wherein the second light source is configured to generate cyan-like second light source light having one or more wavelengths selected from the range of 470-520 nm, wherein the light generating device further optionally comprises a second luminescent material, configured to convert part of one or more of the first light source light and the second light source light into second luminescent material light, wherein the first light source and the second light source are configured upstream of the first luminescent material and the optional second luminescent material, wherein in the first control mode the device light is white light comprising the first light source light, the second light source light, the first luminescent material light and the optional second luminescent material light, and wherein the device light has a color rendering index of at least 80.

10. The light generating device according to claim 9, wherein the first luminescent material light has one or more wavelengths in the yellow wavelength range, and wherein the second luminescent material light has one or more wavelength in the red wavelength range.

11. The light generating device according to claim 1, wherein the second light has a dominant wavelength selected from the range of 474-490 nm.

12. The light generating device according to claim 1, wherein the second light has a spectral power Wopt/1100 lumen, wherein the first light has a correlated color temperature $CCT_{211}$, wherein Wopt/1100 lumen refers to the value of the radiometric contribution in Watt of the second light per 1100 Lumen of device light, wherein $CCT_{211}$ refers to the value of the correlated color temperature in Kelvin of the first light, and wherein a value of Wopt/1100 lumen is selected from the range of: $0.03+0.00019*CCT_{211}*\leq Wopt/1100\ lumen \leq 0.12+0.000208*CCT_{211}$.

13. The light generating device according to claim 2, wherein the first source comprises a first light source configured to generate first light source light comprising the first light, wherein the second source comprises a second light source configured to provide second light source light, and the light generating device further comprising a third light source configured to generate third light source light spectrally different from the second light source light, wherein second light source light has a second peak maximum (λmax2), wherein the third light source light has a third peak maximum (λmax3) differing at least 5 nm, and wherein the second light comprises the second light source light and the third light source light, wherein the second light source comprises a solid state light source, wherein the third light source comprises a solid state light source, and wherein the second light source and the third light source are from different bins, and wherein the second light source and the third light source are controllable, and wherein the second peak maximum (λmax2) is selected from the range of 470-485 nm, and wherein the third peak maximum (λmax3) is selected from the range of 500-510 nm.

14. The light generating device according to claim 1, wherein the first source, the second source, optional further sources of further light, and the first control mode, are chosen to provide the device light with a color point at 3-10 SDCM below the black body locus.

15. A lighting system comprising the light generating device according to claim 1, wherein the spectral distribution of the device light is controllable, the lighting system further comprising a control system and an input device selected from the group consisting of a user interface, a time device, and a sensor, and wherein the control system is configured to control the spectral distribution of the device light in response to a signal of the input device.

* * * * *